(12) United States Patent
Hawes et al.

(10) Patent No.: US 10,671,031 B2
(45) Date of Patent: Jun. 2, 2020

(54) BODY GESTURE CONTROL SYSTEM FOR BUTTON-LESS VAPING

(71) Applicant: Altria Client Services LLC, Richmond, VA (US)

(72) Inventors: Eric Hawes, Midlothian, VA (US); Raymond Lau, Richmond, VA (US); Terry Bache, Richmond, VA (US); Niall Gallagher, Richmond, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 526 days.

(21) Appl. No.: 15/390,810

(22) Filed: Dec. 27, 2016

(65) Prior Publication Data

US 2017/0108840 A1    Apr. 20, 2017

Related U.S. Application Data

(63) Continuation-in-part of application No. 15/135,932, filed on Apr. 22, 2016, now Pat. No. 10,327,474.
(Continued)

(51) Int. Cl.
*A24F 47/00* (2020.01)
*G05B 15/02* (2006.01)
(Continued)

(52) U.S. Cl.
CPC ............ *G05B 15/02* (2013.01); *A24F 47/008* (2013.01); *A61M 11/042* (2014.02); *A61M 15/06* (2013.01); *A61M 15/0021* (2014.02); *A61M 2205/276* (2013.01); *A61M 2205/332* (2013.01); *A61M 2205/3317* (2013.01); *A61M 2205/3334* (2013.01); *A61M 2205/3368* (2013.01); *A61M 2205/52* (2013.01); *A61M 2205/60* (2013.01);
(Continued)

(58) Field of Classification Search
CPC .................................................... A24F 47/008
See application file for complete search history.

(56) References Cited

U.S. PATENT DOCUMENTS 5,666,977 A    9/1997  Higgins et al.
7,699,052 B2   4/2010  Schiewe et al.
(Continued)

FOREIGN PATENT DOCUMENTS

CN        1575673 A      2/2005
CN       203646502 U     6/2014
(Continued)

OTHER PUBLICATIONS

International Preliminary Report on Patentability dated Oct. 24, 2017.
(Continued)

*Primary Examiner* — Eric Yaary
(74) *Attorney, Agent, or Firm* — Harness, Dickey & Pierce, P.L.C.

(57) ABSTRACT

A method of detecting a hand-to-mouth (HMG) gesture with an e-vaping device includes detecting movements of the e-vaping device; generating quaternions based on the detected movements; generating movement features based on the generated quaternions; applying the generated movement features to a classifier; and determining whether the detected movements correspond to an HMG based on an output of the classifier.

11 Claims, 20 Drawing Sheets

Related U.S. Application Data

(60) Provisional application No. 62/151,179, filed on Apr. 22, 2015, provisional application No. 62/151,160, filed on Apr. 22, 2015.

(51) Int. Cl.
  *A61M 15/06* (2006.01)
  *A61M 11/04* (2006.01)
  *A61M 15/00* (2006.01)

(52) U.S. Cl.
  CPC ............... *A61M 2205/6018* (2013.01); *A61M 2205/8212* (2013.01)

(56) References Cited

U.S. PATENT DOCUMENTS

| | | | |
|---|---|---|---|
| 8,205,622 | B2 | 6/2012 | Pan |
| 8,550,069 | B2 | 10/2013 | Alelov |
| 8,820,330 | B2 | 9/2014 | Bellinger et al. |
| 8,977,115 | B2 | 3/2015 | Penman, Jr. |
| 9,072,321 | B2 | 7/2015 | Liu |
| 9,095,175 | B2 | 8/2015 | Terry et al. |
| 2005/0016550 | A1 | 1/2005 | Katase |
| 2008/0092912 | A1 | 4/2008 | Robinson et al. |
| 2009/0266358 | A1 | 10/2009 | Sacristan Rock et al. |
| 2011/0265806 | A1 | 11/2011 | Alarcon et al. |
| 2012/0174914 | A1 | 7/2012 | Pirshafiey et al. |
| 2012/0272194 | A1* | 10/2012 | Yang ............... G06F 3/017 715/863 |
| 2013/0042865 | A1 | 2/2013 | Monsees et al. |
| 2013/0087160 | A1 | 4/2013 | Gherghe |
| 2013/0182360 | A1 | 7/2013 | Stevens et al. |
| 2013/0284192 | A1 | 10/2013 | Peleg et al. |
| 2013/0327327 | A1 | 12/2013 | Edwards et al. |
| 2013/0340775 | A1 | 12/2013 | Juster et al. |
| 2013/0341218 | A1 | 12/2013 | Liu |
| 2014/0007891 | A1 | 1/2014 | Liu |
| 2014/0096781 | A1 | 4/2014 | Sears et al. |
| 2014/0096782 | A1 | 4/2014 | Ampolini et al. |
| 2014/0107815 | A1 | 4/2014 | LaMothe |
| 2014/0123989 | A1 | 5/2014 | LaMothe |
| 2014/0123990 | A1 | 5/2014 | Timmermans |
| 2014/0157583 | A1 | 6/2014 | Ward et al. |
| 2014/0174459 | A1 | 6/2014 | Burstyn |
| 2014/0190830 | A1 | 7/2014 | Sturmer et al. |
| 2014/0224267 | A1 | 8/2014 | Levitz et al. |
| 2014/0246035 | A1 | 9/2014 | Minskoff et al. |
| 2014/0253144 | A1 | 9/2014 | Novak, III et al. |
| 2014/0261408 | A1 | 9/2014 | DePiano et al. |
| 2014/0261495 | A1 | 9/2014 | Novak, III et al. |
| 2014/0270727 | A1 | 9/2014 | Ampolini et al. |
| 2014/0270730 | A1 | 9/2014 | DePiano et al. |
| 2014/0299137 | A1 | 10/2014 | Kieckbusch et al. |
| 2014/0299141 | A1 | 10/2014 | Flick |
| 2014/0338685 | A1 | 11/2014 | Amir |
| 2014/0345635 | A1 | 11/2014 | Rabinowitz et al. |
| 2014/0360517 | A1 | 12/2014 | Taggart et al. |
| 2014/0366898 | A1* | 12/2014 | Monsees ............... A24F 47/008 131/329 |
| 2014/0378790 | A1 | 12/2014 | Cohen |
| 2015/0027455 | A1 | 1/2015 | Peleg et al. |
| 2015/0075546 | A1 | 3/2015 | Kueny, Sr. et al. |
| 2015/0082859 | A1 | 3/2015 | Xiang |
| 2015/0128971 | A1 | 5/2015 | Verleur et al. |
| 2015/0136158 | A1 | 5/2015 | Stevens et al. |
| 2015/0142387 | A1 | 5/2015 | Alarcon et al. |
| 2015/0164430 | A1 | 6/2015 | Hu et al. |
| 2015/0237917 | A1 | 8/2015 | Lord |
| 2015/0257445 | A1 | 9/2015 | Henry, Jr. et al. |
| 2015/0282527 | A1 | 10/2015 | Henry, Jr. |
| 2015/0320116 | A1 | 11/2015 | Bleloch et al. |
| 2015/0374039 | A1 | 12/2015 | Zhu |
| 2016/0000149 | A1 | 1/2016 | Scatterday |
| 2016/0029698 | A1 | 2/2016 | Xiang |
| 2016/0158782 | A1 | 6/2016 | Henry, Jr. et al. |
| 2017/0013883 | A1* | 1/2017 | Han ............... A24F 47/008 |
| 2017/0127979 | A1* | 5/2017 | Azaria ............... A61B 5/1123 |
| 2017/0188946 | A1* | 7/2017 | Klusmann ........... A61M 1/0088 |

FOREIGN PATENT DOCUMENTS

| | | |
|---|---|---|
| CN | 104432537 A | 3/2015 |
| GB | 2502164 A | 11/2013 |
| WO | WO-2014060267 A2 | 4/2014 |
| WO | WO-2014060269 A1 | 4/2014 |
| WO | WO-2014/066730 A1 | 5/2014 |
| WO | WO-2014095737 A1 | 6/2014 |
| WO | WO-2014125483 A1 | 8/2014 |
| WO | WO-2014-144678 A2 | 9/2014 |
| WO | WO-2015052513 A2 | 4/2015 |
| WO | WO-2015077645 A1 | 5/2015 |
| WO | WO-2015131991 A1 | 9/2015 |
| WO | WO-2015189556 A1 | 12/2015 |
| WO | WO-2016/100368 | 6/2016 |

OTHER PUBLICATIONS

Parate, "Designing Efficient and Accurate Behavior-Aware Mobile Systems," Doctoral Dissertations, University of Massachusetts-Amherst, 2014.
International Search Report and Written Opinion dated Mar. 29, 2018.
Office Action for U.S. Appl. No. 15/135,932 dated Mar. 14, 2018.
Office Action for U.S. Appl. No. 15/135,932 dated Sep. 18, 2018.
Notice of Allowance for U.S. Appl. No. 15/135,932 dated Feb. 26, 2019.
Smokio, http://www.premiumlifestyle.co.uk/products/smokio-smart-wireless-e-cigarette, 2014.
Go Electronic Cigarette, "Igo 4Electronic Cigarette," http://www.electronic-cigarette.ie/Charger-iGO4, Feb. 19, 2015.
International Search Report and Written Opinion dated Jul. 19, 2016.
European Examination Report dated Jul. 9, 2019.
Eurasian Office Action for corresponding Application No. 201792100 dated Jun. 27, 2019.
Chinese Office Action and English translation thereof dated Sep. 27, 2019.
Eurasian Office Action dated Jan. 21, 2020 in Eurasian Application No. 201792100.
Ukrainian Office Action and English translation thereof dated Mar. 26, 2020.

* cited by examiner

108

110

112

118

120

208

209

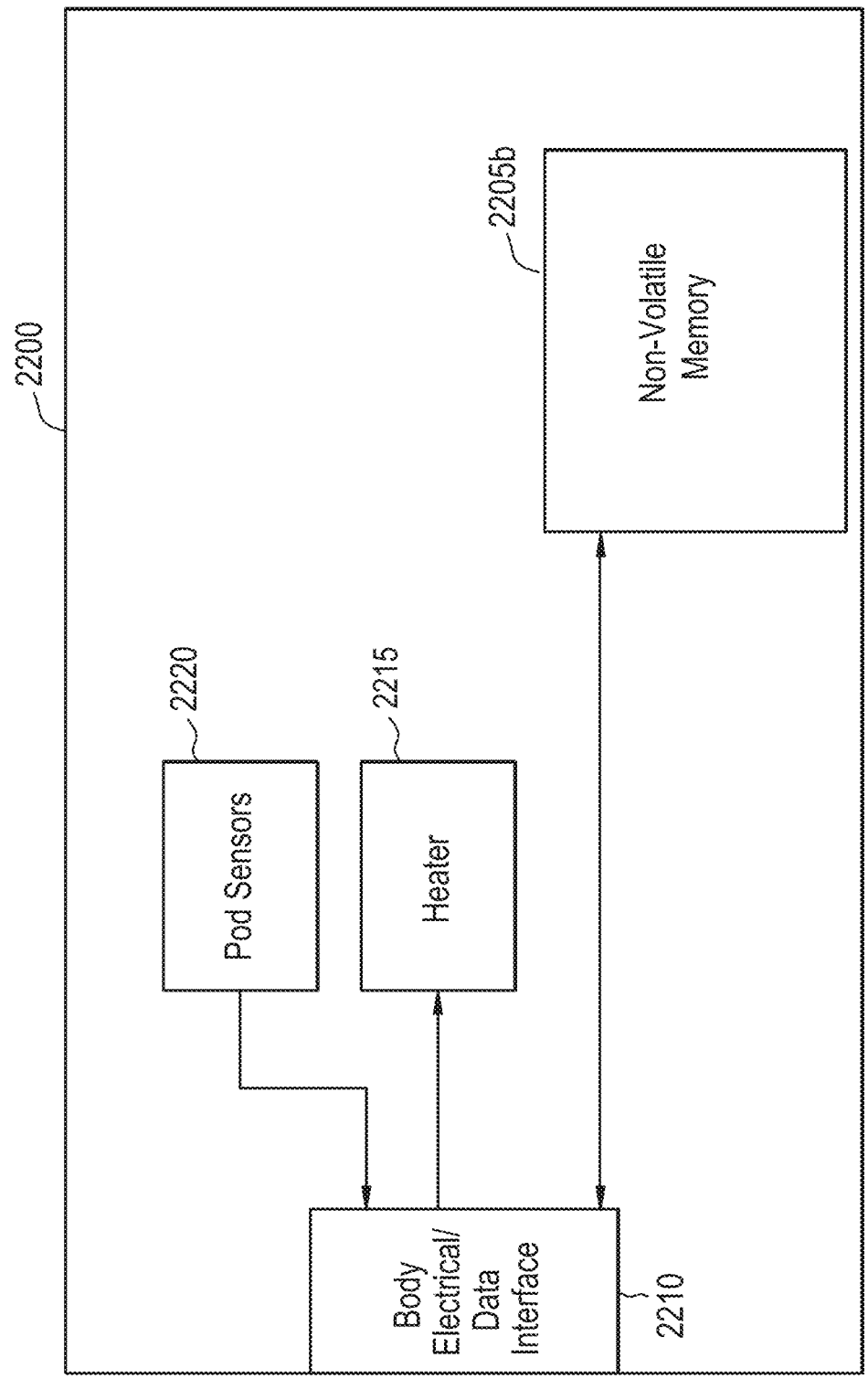

BODY GESTURE CONTROL SYSTEM FOR BUTTON-LESS VAPING

PRIORITY

This non-provisional patent application is a continuation-in-part of U.S. patent application Ser. No. 15/135,932 which was filed on Apr. 22, 2016 in the United States Patent and Trademark Office and claims priority under 35 U.S.C. § 119(e) to provisional U.S. application Nos. 62/151,160 filed on Apr. 22, 2015 and 62/151,179 filed on Apr. 22, 2015, both in the United States Patent and Trademark Office, the entire contents of each of which are incorporated herein by reference.

BACKGROUND

Field

The present disclosure relates to electronic vapor devices including self-contained articles including pre-vapor formulations.

Description of Related Art

Electronic vaping devices are used to vaporize a pre-vapor formulation material into a vapor. These electronic vaping devices may be referred to as e-vaping devices. E-vaping devices include a heater which vaporizes the pre-vapor formulation material to produce vapor. An e-vaping device may include several e-vaping elements including a power source, a cartridge or e-vaping tank including the heater and along with a reservoir capable of holding the pre-vapor formulation material.

SUMMARY

According to at least some example embodiments, a method of detecting a hand-to-mouth (HMG) gesture with an e-vaping device includes detecting movements of the e-vaping device; generating quaternions based on the detected movements; generating movement features based on the generated quaternions; applying the generated movement features to a classifier; and determining whether the detected movements correspond to an HMG based on an output of the classifier.

The HMG may be a gesture in which an adult vaper holding the e-vaping device moves their hand towards their mouth, and the classifier is trained to distinguish HMGs from other gestures.

The classifier may be a classifier that was generated through training using linear discriminant analysis (LDA).

The method may further include transforming the quaternions into three-dimensional (3-D) Cartesian coordinates.

The generating movement features based on the generated quaternions may include extracting the movement features based on the 3-D Cartesian coordinates.

The method may further include filtering the 3-D Cartesian coordinates, and the extracting may further include extracting the movement features from the filtered 3-D Cartesian coordinates.

The method may further include filtering the quaternions, the transforming may further include transforming the filtered quaternions into the three-dimensional (3-D) Cartesian coordinates, and the extracting may further include extracting the movement features from the 3-D Cartesian coordinates.

The generated movement features may include a linear speed of the e-vaping device, and a distance from rest point location of the e-vaping device.

The distance from rest point location of the e-vaping device may be a distance between a current location of the e-vaping device and a rest point of the e-vaping device, the rest point being a point in three-dimensional (3-D) space at which the e-vaping device was last stationary or substantially stationary.

The detecting movements may include detecting the movements of the e-vaping device using device sensors included in the e-vaping device, the device sensors including at least one of a gyroscope, an accelerometer, and a magnetometer.

The detecting movements may include detecting the movements of the e-vaping device using an inertial measurement unit (IMU) included in the e-vaping device.

According to at least some example embodiments, a method of controlling a heater of an e-vaping device, the heater having at least a first operation mode in which a first amount of power is supplied to the heater by the e-vaping device, and a second operation mode in which a second amount of power greater than the first amount is supplied to the heater by the e-vaping device, includes detecting movements of the e-vaping device; determining whether a hand-to-mouth gesture (HMG) occurred with respect to the e-vaping device based on the detected movements; and transitioning the operation mode of the heater from the first operation mode to the second operation mode in response to determining that the HMG occurred.

The first operation mode may be a mode in which no power is supplied to the heater by the e-vaping device, and the second operation mode may be a mode in which an amount of power supplied to the heater by the e-vaping device is an amount that causes the heater to heat a pre-vapor formulation stored in the e-vaping device to a temperature below a boiling point of the pre-vapor formulation.

The method may further include generating quaternions based on the detected movements; generating movement features based on the generated quaternions; and applying the generated movement features to a classifier, and the determining may include determining whether the HMG occurred based on an output of the classifier.

The HMG is a gesture in which an adult vaper holding the e-vaping device moves their hand towards their mouth, and the classifier is trained to distinguish HMGs from other gestures.

The classifier may be a classifier that was generated through training using linear discriminant analysis (LDA).

The method may further include transforming the quaternions into three-dimensional (3-D) Cartesian coordinates.

The generating movement features based on the generated quaternions may include extracting the movement features based on the 3-D Cartesian coordinates.

The method may further include filtering the 3-D Cartesian coordinates, and the extracting may include extracting the movement features from the filtered 3-D Cartesian coordinates.

The method may further include filtering the quaternions, the transforming may include transforming the filtered quaternions into the three-dimensional (3-D) Cartesian coordinates, and the extracting may include extracting the movement features from the 3-D Cartesian coordinates.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 22B illustrates an example of the pod system of FIG. 22A in which a cryptographic coprocessor is omitted, according to an example embodiment.

DETAILED DESCRIPTION

Figure 1:
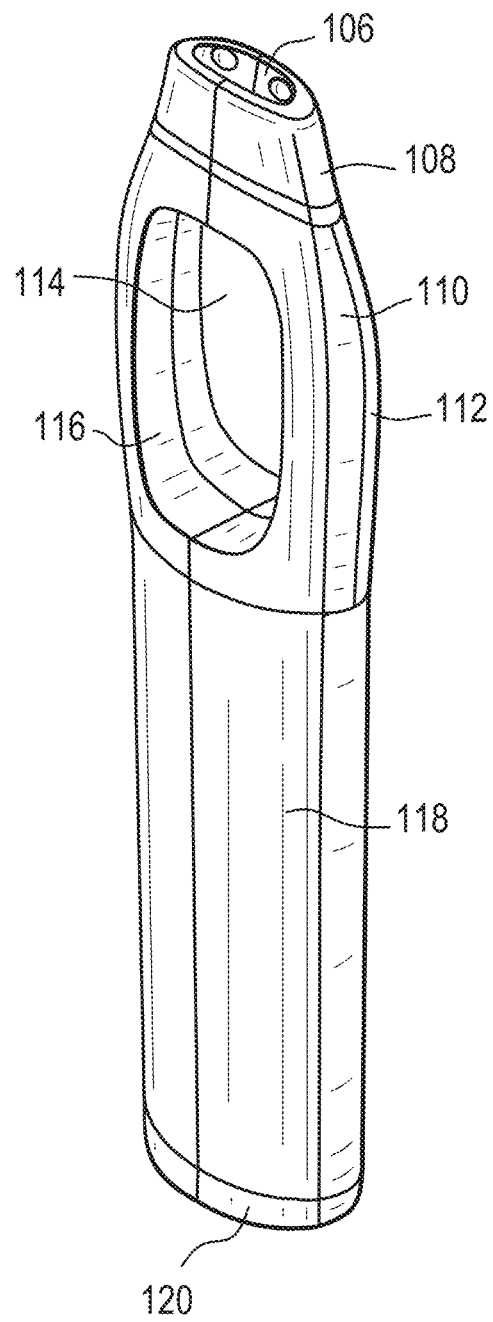
FIG. 1 is a perspective view of a dispensing body of an e-vapor apparatus according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and/or sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including,", "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

An "e-vapor device" as used herein may be referred to on occasion using, and considered synonymous with, any of the terms: e-vaping device, e-vapor apparatus, and e-vaping apparatus.

FIG. 1 is a perspective view of a dispensing body of an e-vapor apparatus according to an example embodiment. Referring to FIG. 1, a dispensing body 104 of an e-vapor apparatus includes a frame portion that is connected to a body portion 118. The frame portion includes a first frame 110 and a second frame 112. The side walls 116 (e.g., inner side surfaces) of the first frame 110 and the second frame 112 define a through-hole 114. The through-hole 114 is configured to receive a pod assembly (which will be subsequently discussed in detail).

Generally, an e-vapor apparatus may include the dispensing body 104, a pod assembly inserted in the through-hole 114 of the dispensing body 104, and a vaporizer disposed in at least one of the pod assembly and the dispensing body 104. The pod assembly may include a pre-vapor formulation compartment (e.g., pre-vapor formulation compartment), a device compartment, and a vapor channel. The vapor channel may extend from the device compartment and traverse the pre-vapor formulation compartment. The pre-vapor formulation compartment is configured to hold a pre-vapor formulation (e.g., pre-vapor formulation) therein. A pre-vapor formulation is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol.

The dispensing body 104 includes a proximal portion and an opposing distal portion. The mouthpiece 108 is disposed at the proximal portion, while the end piece 120 is disposed at the distal portion. The proximal portion includes a vapor passage 106 and the through-hole 114. The vapor passage 106 extends from an end surface of the proximal portion to the side wall 116 of the through-hole 114. The vapor passage 106 is in the form of one or more passageways extending through the proximal portion of the dispensing body 104. The through-hole 114 is between the vapor passage 106 and the distal portion of the dispensing body 104 (e.g., between the mouthpiece 108 and the body portion 118).

A vaporizer (which will be subsequently discussed in more detail) is disposed in at least one of the pod assembly and the dispensing body 104. The pre-vapor formulation compartment of the pod assembly is configured to be in fluidic communication with the vaporizer during an operation of the e-vapor apparatus such that the pre-vapor formulation from the pre-vapor formulation compartment comes into thermal contact with the vaporizer. The vaporizer is configured to heat the pre-vapor formulation to produce a vapor that passes through the pod assembly via the vapor channel. The through-hole 114 of the dispensing body 104 is configured to receive the pod assembly such that the vapor channel of the pod assembly is aligned with the vapor passage 106 of the dispensing body 104 so as to facilitate a delivery of the vapor through the vapor passage 106 of the dispensing body 104.

Figure 2:
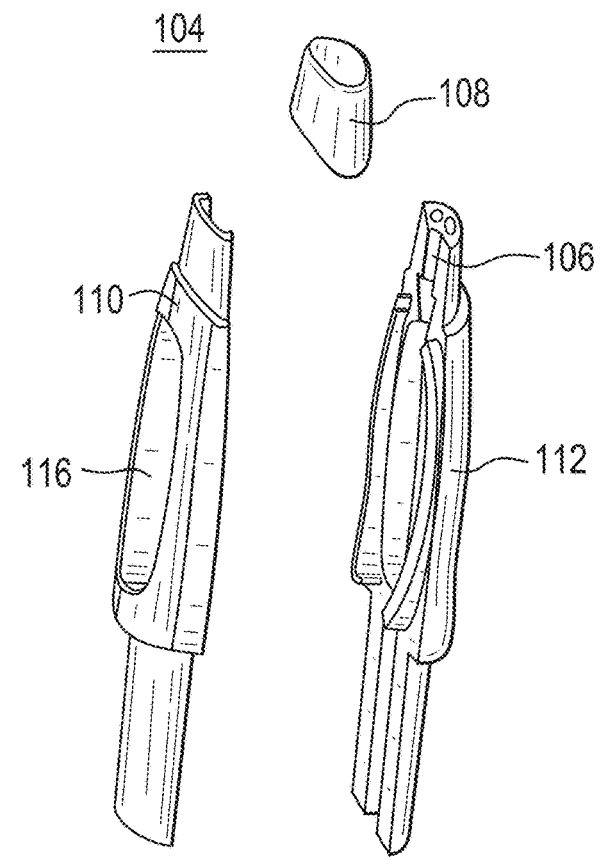
FIG. 2 is an exploded view of the dispensing body of FIG. 1.
Figure 2:
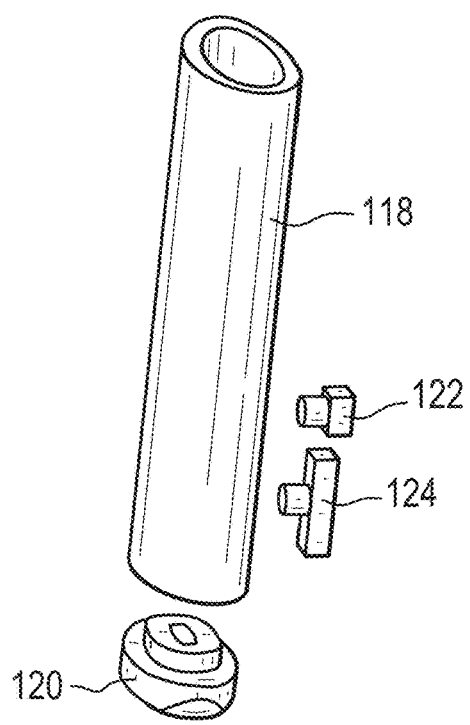

FIG. 2 is an exploded view of the dispensing body of FIG. 1. Referring to FIG. 2, the first frame 110 and the second frame 112 are configured to unite to form the frame portion of the dispensing body 104. A number of options are available for uniting the first frame 110 and the second frame 112. In an example embodiment, the first frame 110 is a female member, while the second frame 112 is a male member that is configured to engage therewith. Alternatively, the first frame 110 may be a male member, while the second frame 112 may be a female member that is configured to engage therewith. The engagement of the first frame 110 and the second frame 112 may be via a snap-fit, friction-fit, or slide-lock type arrangement, although example embodiments are not limited thereto.

The first frame 110 may be regarded as the front frame of the dispensing body 104, and the second frame 112 may be regarded as the rear frame (or vice versa). Additionally, the proximal ends of the first frame 110 and the second frame 112, when united, define the vapor passage 106 therebetween. The vapor passage 106 may be in the form of a single passageway that is in communication with the through-hole 114 defined by the side wall 116. Alternatively, the vapor passage 106 may be in the form of a plurality of passageways that are in communication with the through-hole 114 defined by the side wall 116. In such an example, the plurality of passageways may include a central passageway surrounded by peripheral passageways (or just several evenly spaced passageways). Each of the plurality of passageways may independently extend from the through-hole 114 to the proximal end surface of the frame portion. Alternatively, a common passageway may extend partly from the through-hole 114 and then branch into a plurality of passageways that extend to the proximal end surface of the frame portion.

The mouthpiece 108 is configured to slip onto the proximal end of the frame portion that defines the vapor passage 106. As a result, the outer surface of the proximal end formed by the first frame 110 and the second frame 112 may correspond to an inner surface of the mouthpiece 108. Alternatively, the proximal end defining the vapor passage 106 may be integrally formed as part of the mouthpiece 108 (instead of being a part of the frame portion). The mouthpiece 108 may be secured via a snap-fit type or other suitable arrangement. In an example embodiment, the mouthpiece 108 is a removable element that is intended to permit voluntary, recommended, or required replacement by an adult vaper. For instance, the mouthpiece 108 may, in addition to its intended functionality, provide a visual or other sensory appeal. In particular, the mouthpiece 108 may be formed of an ornamental material (e.g., wood, metal, ceramic) and/or include designs (e.g., patterns, images, characters). Moreover, the length of the mouthpiece 108 may be varied to adjust for the temperature at an outlet of the mouthpiece. Thus, the mouthpiece 108 may be customized so as to provide an expression of personality and individuality. In other instances, the removable nature of the mouthpiece 108 may facilitate a recommended replacement due to the amount of usage or a required replacement due to wear over time or damage (e.g., chipped mouthpiece 108 caused by accidental dropping of e-vapor apparatus).

The lower ends of the first frame 110 and the second frame 112 opposite the proximal ends (that define the vapor passage 106) are configured to insert into the body portion 118. To facilitate a secure fit, the outer surface of the lower ends of the first frame 110 and the second frame 112 may correspond to a receiving inner surface of the body portion 118. Additionally, the lower ends of the first frame 110 and the second frame 112 may also define a groove therebetween to accommodate one or more wires that connect to one or more electrical contacts provided in the side wall 116 (e.g., lower surface of the side wall 16 opposite the vapor passage 106). A power source (e.g., battery) may also be provided in the groove to supply the requisite current through the wire(s). Alternatively, the power source may be provided in an available space within the body portion 118 between the inserted lower end of the frame portion and the end piece 120.

A first button 122 and a second button 124 may be provided on the body portion 118 and connected to the corresponding circuitry and electronics therein. In an example embodiment, the first button 122 may be a power button, and the second button 124 may be a battery level indicator. The battery level indicator may display a representation of the amount of power available (e.g., 3 out of 4 bars). In addition, the battery level indicator may also blink and/or change colors. To stop the blinking, a second button 124 may be pressed. Thus, the button(s) of the e-vapor apparatus may have a control and/or display function. It should be understood that the examples with regard to the first button 122 and the second button 124 are not intended to be limiting and can have different implementations depending on the desired functionalities. Accordingly, more than two buttons (and/or of different shapes) may be provided in the same proximity or at a different location on the e-vapor apparatus. Moreover, different implementations of the first button 122 and the second button 124 may be controlled by a controller 2105 based on inputs from an adult vaper.

Figure 3:
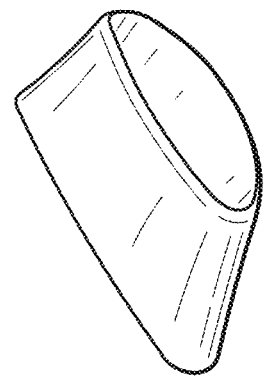
FIG. 3 is a perspective view of the mouthpiece of FIG. 2.

FIG. 3 is a perspective view of the mouthpiece of FIG. 2. Referring to FIG. 3, the mouthpiece 108 may be an open-ended cap-like structure that is configured to slip onto the proximal end of the frame portion defining the vapor passage 106. The mouthpiece 108 may have a wider base that tapers to a narrower top. However, it should be understood that example embodiments are not limited thereto. In an example embodiment, one side of the mouthpiece 108 may be more linear, while the opposing side may be more curved.

Figure 4:
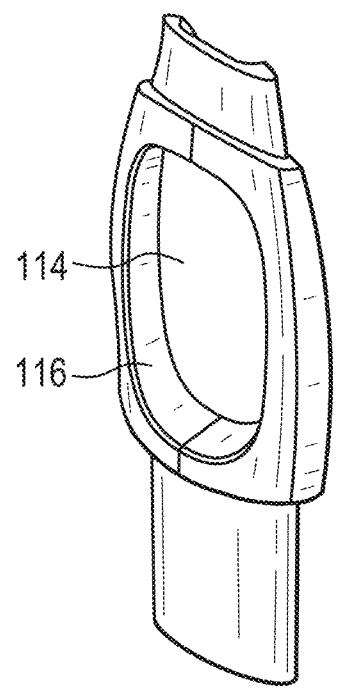
FIG. 4 is a perspective view of the first frame of FIG. 2.

FIG. 4 is a perspective view of the first frame of FIG. 2. Referring to FIG. 4, the first frame 110 includes a side wall 116 that defines a through-hole 114. The first frame 110 is configured to unite with the second frame 112, which also includes a side wall 116 defining a through-hole 114. Because the combined through-hole 114 is configured to receive a pod assembly, the side walls 116 of the first frame 110 and the second frame 112 may form a relatively smooth and continuous surface to facilitate the insertion of the pod assembly.

Figure 5:
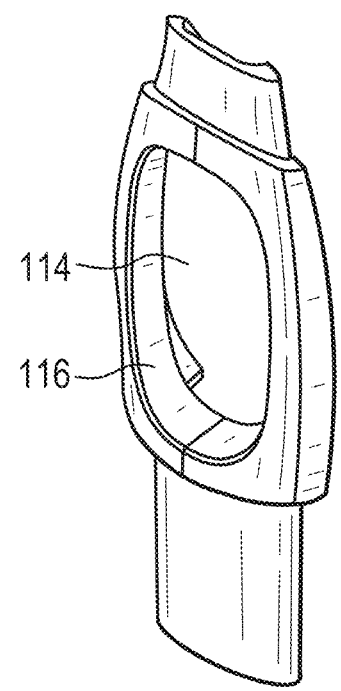
FIG. 5 is a perspective view of the second frame of FIG. 2.

FIG. 5 is a perspective view of the second frame of FIG. 2. Referring to FIG. 5, the second frame 112 is configured to unite with the first frame 110 such that the shape defined by the combined side walls 116 corresponds to the shape of the side surface of a pod assembly. In addition, an attachment structure (e.g., mating member/recess, magnetic arrangement) may be provided on at least one of the side walls 116 and the side surface of the pod assembly.

For example, the attachment structure may include a mating member that is formed on the side wall 116 (of the first frame 110 and/or second frame 112) and a corresponding recess that is formed on the side surface of the pod assembly. Conversely, the mating member may be formed on the side surface of the pod assembly, while the corresponding recess may be formed on the side wall 116 (of the first frame 110 and/or second frame 112). In a non-limiting embodiment, the mating member may be a rounded structure to facilitate the engagement/disengagement of the attachment structure, while the recess may be a concave indentation that corresponds to the curvature of the rounded structure. The mating member may also be spring-loaded so as to retract (via spring compression) when the pod assembly is being inserted into the through-hole 114 and protract (via spring decompression) when mating member becomes aligned with the corresponding recess. The engagement of the mating member with the corresponding recess may result in an audible click, which provides a notification that the pod assembly is secured and properly positioned within the through-hole 114 of the dispensing body 104.

In another example, the attachment structure may include a magnetic arrangement. For instance, a first magnet may be arranged in the side wall 116 (of the first frame 110 and/or second frame 112), and a second magnet may be arranged in the side surface of the pod assembly. The first and/or second magnets may be exposed or hidden from view behind a layer of material. The first and second magnets are oriented so as to be attracted to each other, and a plurality of pairs of the first and second magnets may be provided to ensure that the pod assembly will be secure and properly aligned within the through-hole 114 of the dispensing body 104. As a result, when the pod assembly is inserted in the through-hole 114, the pair(s) of magnets (e.g., first and second magnets) will be attracted to each other and, thus, hold the pod assembly within the through-hole 114 while properly aligning the channel outlet of the pod assembly with the vapor passage 106 of the dispensing body 104.

Figure 6:
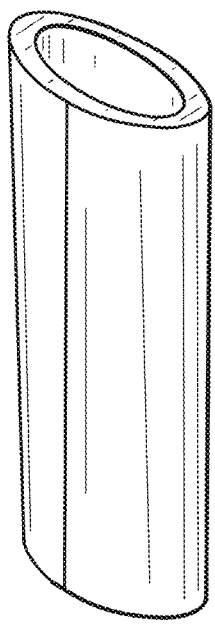
FIG. 6 is a perspective view of the body portion of FIG. 2.

FIG. 6 is a perspective view of the body portion of FIG. 2. Referring to FIG. 6, the body portion 118 may be a tube-like structure that constitutes a substantial segment of the dispensing body 104. The cross-section of the body portion 118 may be oval-shaped, although other shapes are possible depending on the structure of the frame portion. The e-vapor apparatus may be held by the body portion 118. Accordingly, the body portion 118 may be formed of (or covered with) a material that provides enhanced gripping and/or texture appeal to the fingers.

Figure 7:
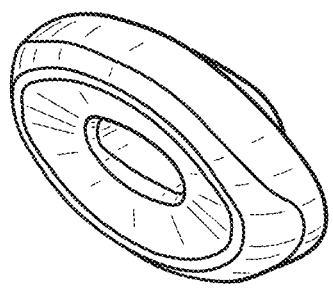
FIG. 7 is a perspective view of the end piece of FIG. 2.

FIG. 7 is a perspective view of the end piece of FIG. 2. Referring to FIG. 7, the end piece 120 is configured to be inserted in the distal end of the body portion 118. The shape of the end piece 120 may correspond to the shape of the distal end of the body portion 118 so as to provide a relatively smooth and continuous transition between the two surfaces.

Figure 8:
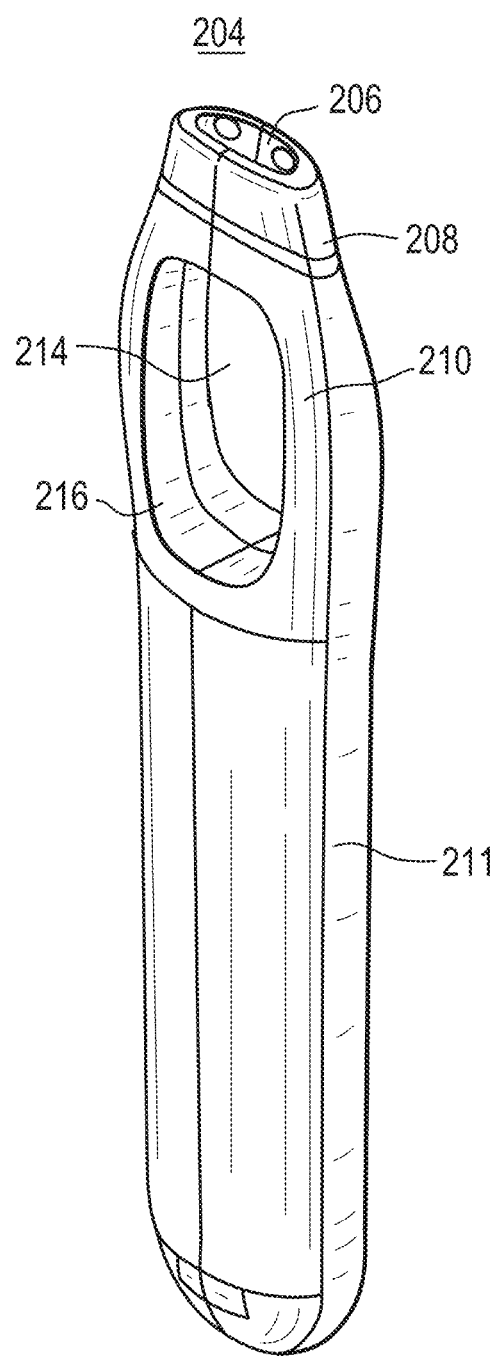
FIG. 8 is a perspective view of another dispensing body of an e-vapor apparatus according to an example embodiment.

FIG. 8 is a perspective view of another dispensing body of an e-vapor apparatus according to an example embodiment. Referring to FIG. 8, the dispensing body 204 includes a side wall 216 defining a through-hole 214 that is configured to receive a pod assembly. A substantial portion of the framework of the dispensing body 204 is provided by the first frame 210, the frame trim 211, and the second frame 212 (e.g., FIG. 9). A vapor passage 206 and a first mouthpiece 208 are provided at a proximal portion of the dispensing body 204.

Figure 9:
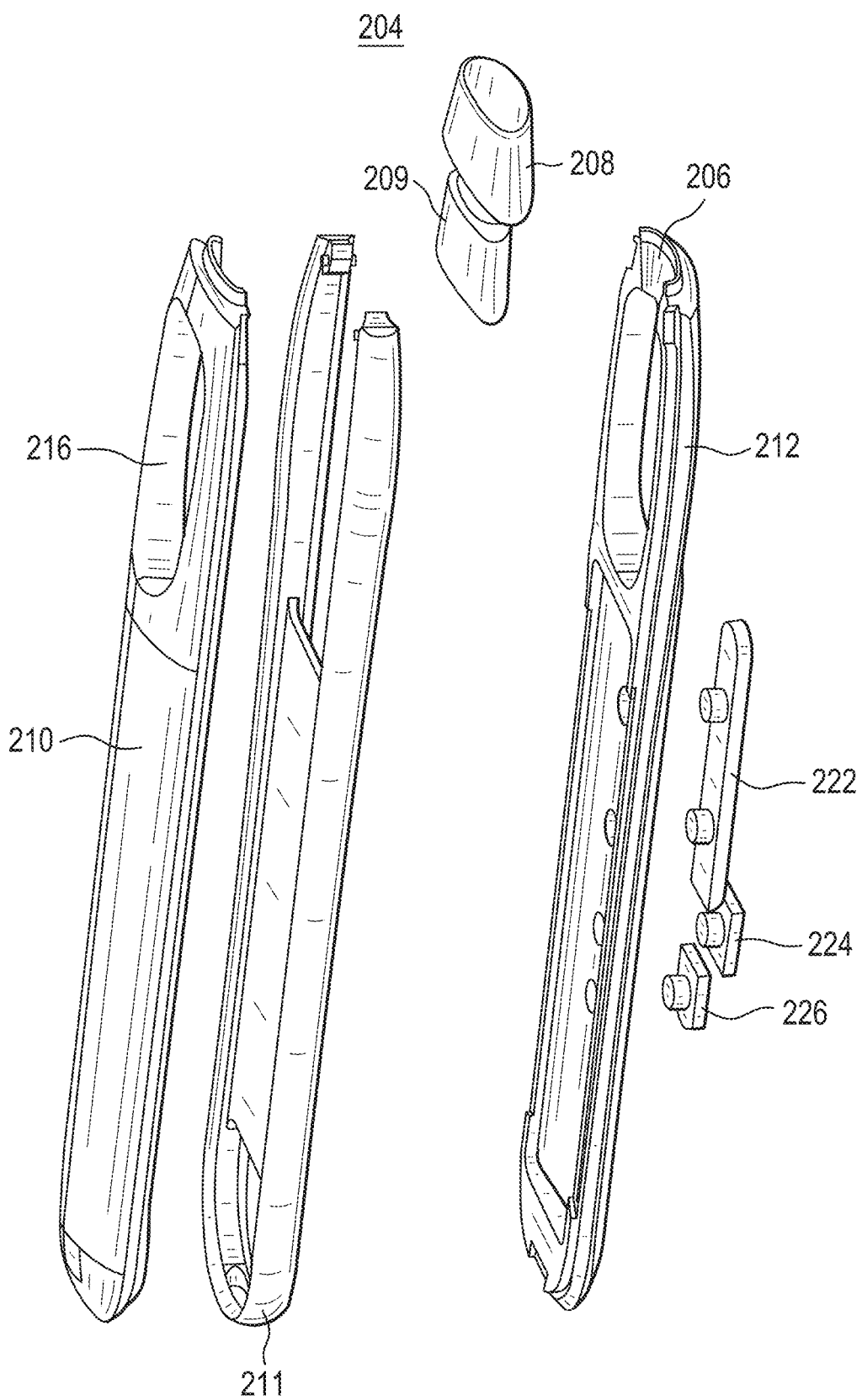
FIG. 9 is an exploded view of the dispensing body of FIG. 8.

FIG. 9 is an exploded view of the dispensing body of FIG. 8. Referring to FIG. 9, the frame trim 211 is sandwiched between the first frame 210 and the second frame 212. However, it should be understood that it is possible to modify and structure the first frame 210 and the second frame 212 such that the frame trim 211 is not needed. The vapor passage 206 may be defined by both the proximal ends of the first frame 210 and the second frame 212 as well as the second mouthpiece 209. As a result, the vapor passage 206 extends from the side wall 216 to the outlet end of the second mouthpiece 209. The first mouthpiece 208 is configured to slip onto the second mouthpiece 209. In an example embodiment, the first mouthpiece 208 may be structured to be removable, while the second mouthpiece 209 may be structured to be permanent. Alternatively, the first mouthpiece 208 may be integrated with the second mouthpiece 209 to form a single structure that is removable.

A first button 222, a second button 224, and a third button 226 may be provided on the second frame 212 of the dispensing body 204. In an example embodiment, the first button 222 may be a display (e.g., battery level indicator), the second button 224 may control an amount of pre-vapor formulation available to the heater, and the third button 226 may be the power button. However, it should be understood that example embodiments are not limited thereto. For example, the third button 226 may be a capacitive slider. Notably, the buttons can have different implementations depending on the desired functionalities. Accordingly, a different number of buttons (and/or of different shapes) may be provided in the same proximity or at a different location on the e-vapor apparatus. Furthermore, the features and considerations in connection with the dispensing body 104 that are also applicable to the dispensing body 204 may be as discussed supra in connection with the dispensing body 104.

Figure 10:
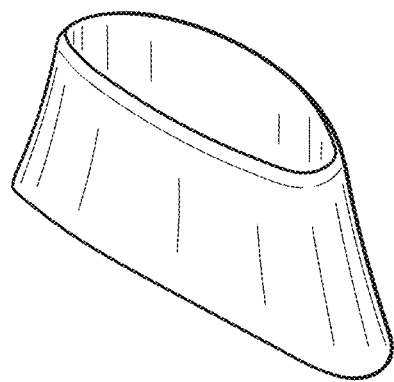
FIG. 10 is a perspective view of the first mouthpiece of FIG. 9.

FIG. 10 is a perspective view of the first mouthpiece of FIG. 9. Referring to FIG. 10, the first mouthpiece 208 is configured to fit over the second mouthpiece 209. Thus, the inner surface of the first mouthpiece 208 may correspond to an outer surface of the second mouthpiece 209.

Figure 11:
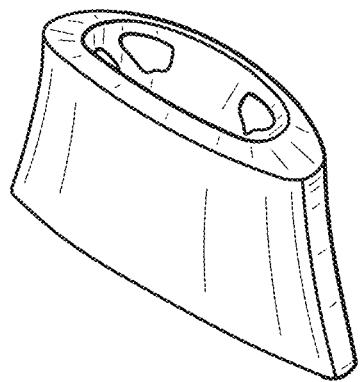
FIG. 11 is a perspective view of the second mouthpiece of FIG. 9.

FIG. 11 is a perspective view of the second mouthpiece of FIG. 9. Referring to FIG. 11, the second mouthpiece 209 defines a vapor passage 206 therein. The second mouthpiece 209 may resemble the combined proximal ends of the first frame 110 and the second frame 112 that define the vapor passage 106 of the dispensing body 104.

Figure 12:
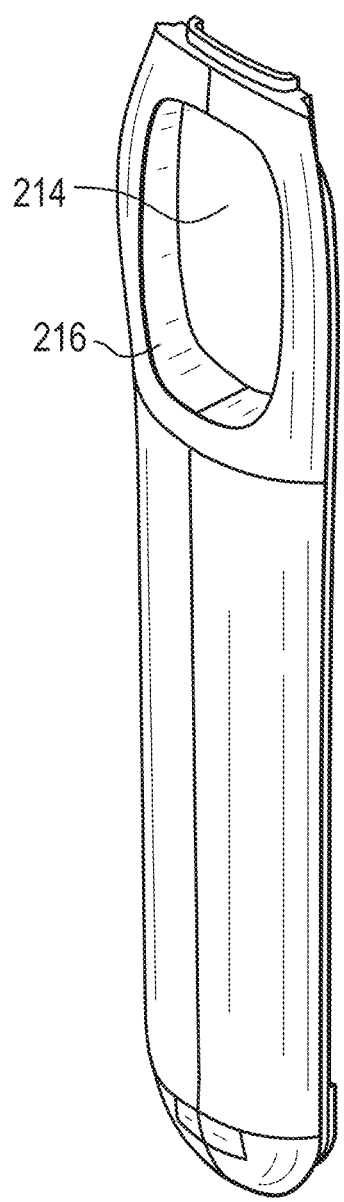
FIG. 12 is a perspective view of the first frame of FIG. 9.

FIG. 12 is a perspective view of the first frame of FIG. 9. Referring to FIG. 12, the first frame 210 includes a side wall 216 that defines a through-hole 214. The top end of the first frame 210 may include a connection structure that facilitates the connection of at least the second mouthpiece 209 thereto.

Figure 13:
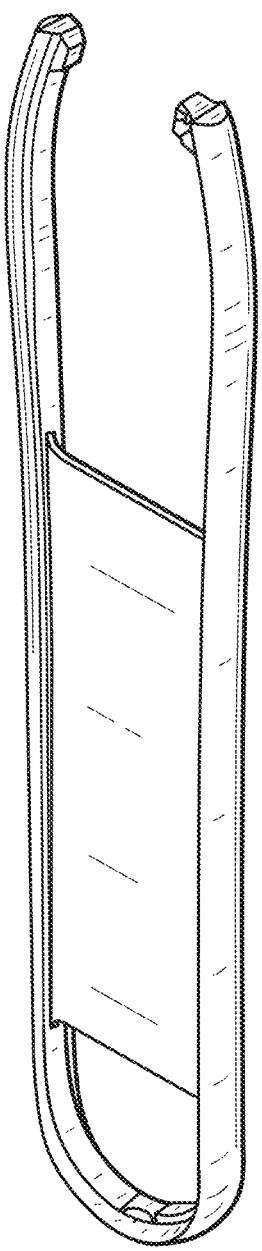
FIG. 13 is a perspective view of the frame trim of FIG. 9.

FIG. 13 is a perspective view of the frame trim of FIG. 9. Referring to FIG. 13, the frame trim 211 may be in the form of a curved strip that is supported by a central plate. When arranged between the first frame 210 and the second frame 212, the frame trim 211 forms a side surface of the dispensing body 204, although example embodiments are not limited thereto.

Figure 14:
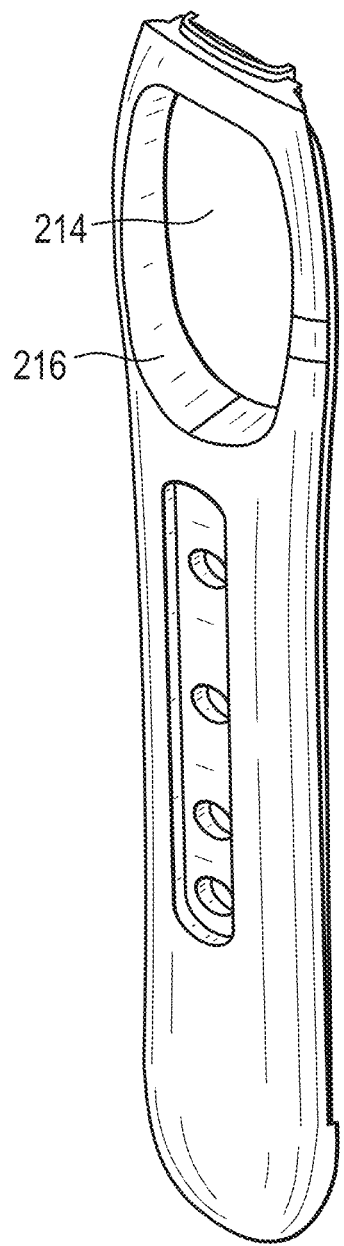
FIG. 14 is a perspective view of the second frame of FIG. 9.

FIG. 14 is a perspective view of the second frame of FIG. 9. Referring to FIG. 14, the second frame 212 includes a side wall 216 that defines a through-hole 214. The top end of the second frame 212 may include a connection structure that facilitates the connection of at least the second mouthpiece 209 thereto. In addition, the surface of the second frame 212 may be provided with a pattern or textured appearance. Such patterning and texturing may be aesthetic (e.g., visually appealing) and/or functional (e.g., enhanced grip) in nature. Although not shown, the surface of the first frame 210 may be similarly provided.

Figure 15:
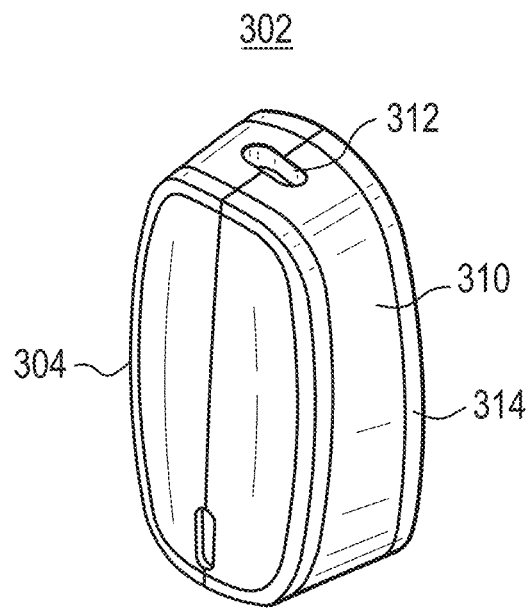
FIG. 15 is a perspective view of a pod assembly of an e-vapor apparatus according to an example embodiment.

FIG. 15 is a perspective view of a pod assembly of an e-vapor apparatus according to an example embodiment. Referring to FIG. 15, the pod assembly 302 includes a pod trim 310 that is arranged between a first cap 304 and a second cap 314. The first cap 304 may be regarded as a front cap, and the second cap 314 may be regarded as a rear cap (or vice versa). The first cap 304 and the second cap 314 may be formed of a transparent material to permit a viewing of the contents (e.g., pre-vapor formulation) in the pod assembly 302. The pod trim 310 defines a channel outlet 312 for the release of vapor generated within the pod assembly 302.

The pod assembly 302 is a self-contained article that can be sealed with a protective film that wraps around the pod trim 310. Additionally, because of the closed system nature of the pod assembly 302, the risk of tampering and contamination can be reduced. Also, the chance of unwanted physical exposure to the pre-vapor formulation within the pod assembly 302 (e.g., via a leak) can be reduced. Furthermore, the pod assembly 302 can be structured so as to prevent refilling.

Figure 16:
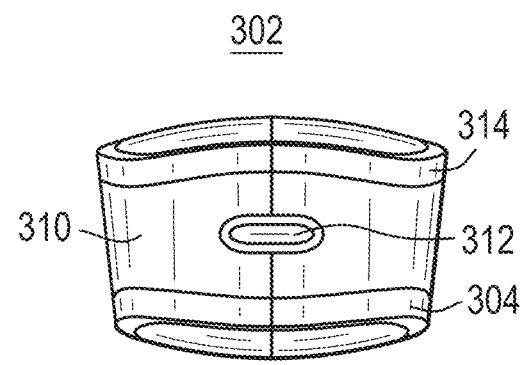
FIG. 16 is a top view of the pod assembly of FIG. 15.

FIG. 16 is a top view of the pod assembly of FIG. 15. Referring to FIG. 16, the second cap 314 is wider than the first cap 304. As a result, the pod trim 310 may slant outwards from the first cap 304 to the second cap 314. However, it should be understood that other configurations are possible depending on the design of the pod assembly 302.

Figure 17:
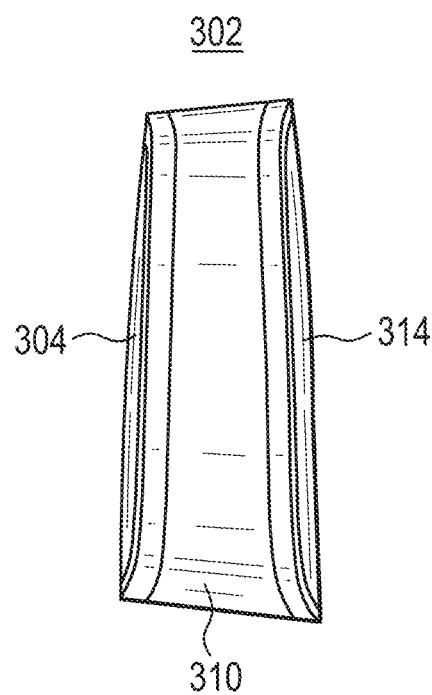
FIG. 17 is a side view of the pod assembly of FIG. 15.

FIG. 17 is a side view of the pod assembly of FIG. 15. Referring to FIG. 17, the second cap 314 is longer than the first cap 304. As a result, the pod trim 310 may slant outwards from the first cap 304 to the second cap 314. As a result, the pod assembly 302 may be inserted in a dispensing body such that the side corresponding to the first cap 304 is received in the through-hole first. In an example embodiment, the pod assembly 302 may be inserted in the through-hole 114 of the dispensing body 104 and/or the through-hole 214 of the dispensing body 204.

Figure 18:
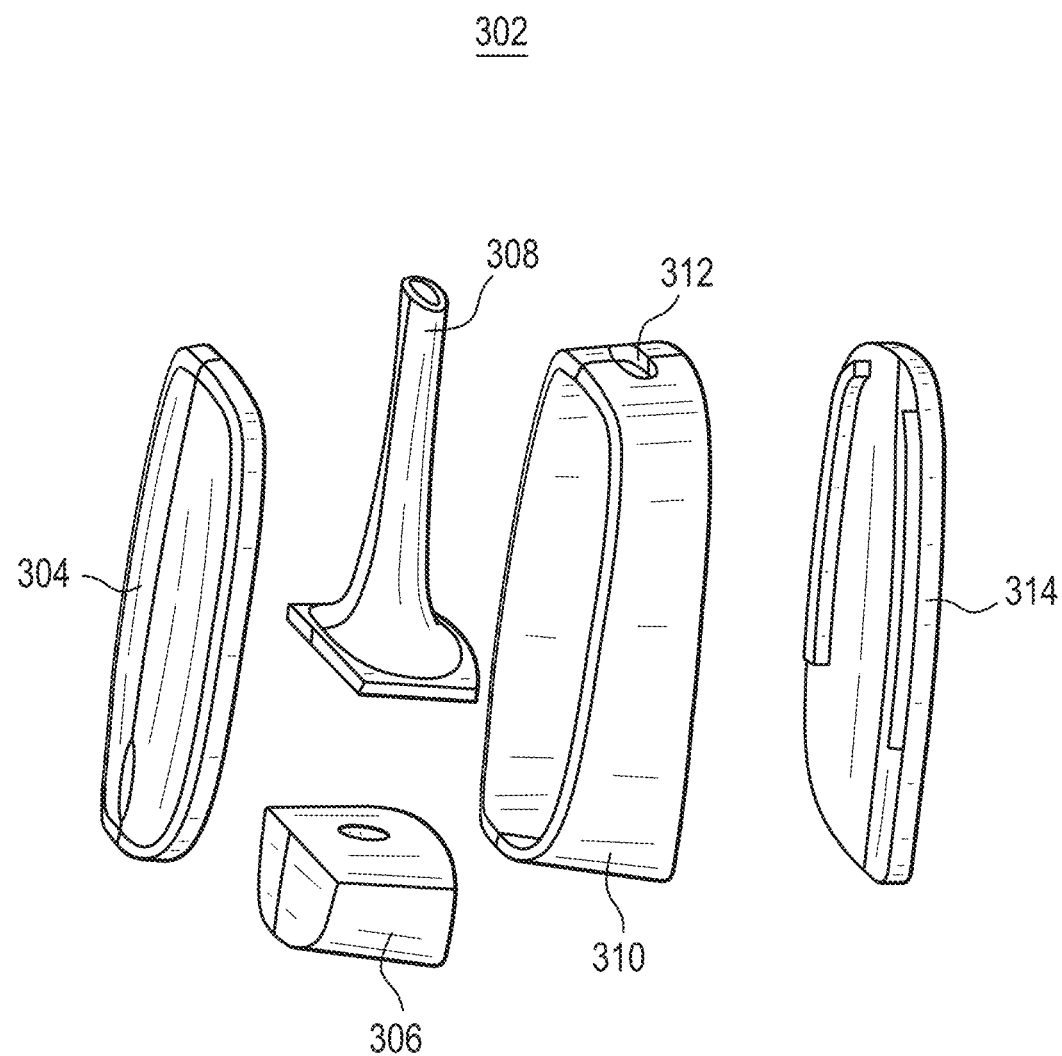
FIG. 18 is an exploded view of the pod assembly of FIG. 15.

FIG. 18 is an exploded view of the pod assembly of FIG. 15. Referring to FIG. 18, the internal space of the pod assembly 302 may be divided into a plurality of compartments by virtue of the elements therein. For instance, the tapered outlet of the vapor channel 308 may be aligned with the channel outlet 312, and the space bounded by the first cap 304, the vapor channel 308, the pod trim 310, and the second cap 314 may be regarded as the pre-vapor formulation compartment. Additionally, the bounded space under the vapor channel 308 may be regarded as the device compartment. For instance, the device compartment may include the vaporizer 306. One benefit of including the vaporizer 306 in the pod assembly 302 is that the vaporizer 306 will only be used for the amount of pre-vapor formulation contained within the pre-vapor formulation compartment and, thus, will not be overused.

Figure 19:
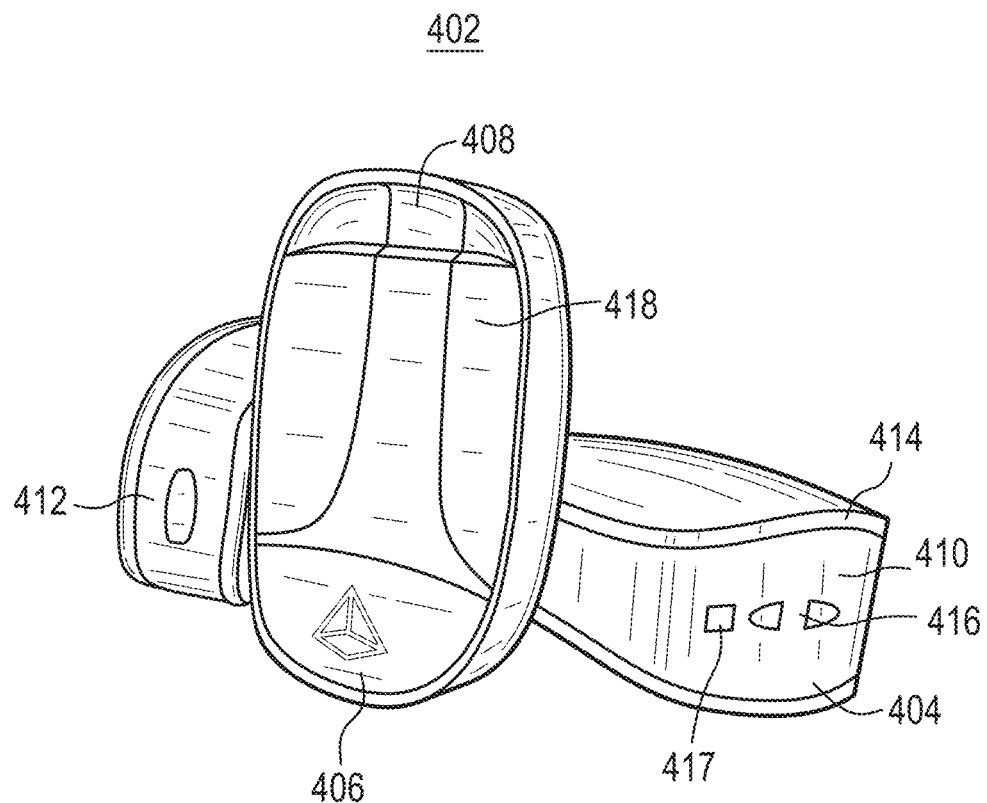
FIG. 19 a perspective view of several pod assemblies according to an example embodiment.

FIG. 19 a perspective view of several pod assemblies according to an example embodiment. Referring to FIG. 19, each of the pod assemblies 402 includes a pod trim 410 arranged between a first cap 404 and a second cap 414. The vapor channel 408 is aligned with the channel outlet 412 and arranged above the vaporizer 406. The pod assembly 402 is sealed to hold a pre-vapor formulation 418 therein and to preclude tampering therewith. The pre-vapor formulation compartment of the pod assembly 402 is configured to hold the pre-vapor formulation 418, and the device compartment includes the vaporizer 406. The pod assembly 402 includes battery contacts 416 and a data connection 417 connected to a non-volatile memory (NVM) or, alternatively, a cryptographic coprocessor with non-volatile memory (CC-NVM) within the pod assembly 402.

The term CC-NVM may refer to a hardware module(s) including a processor for encryption and related processing.

In further detail, the pod assembly 402 for an e-vapor apparatus may include a pre-vapor formulation compartment configured to hold a pre-vapor formulation 418 therein. A device compartment is in fluidic communication with the pre-vapor formulation compartment. The device compartment includes a vaporizer 406. A vapor channel 408 extends from the device compartment and traverses the pre-vapor formulation compartment.

The pod assembly 402 is configured for insertion into a dispensing body. As a result, the dimensions of the pod assembly 402 may correspond to the dimensions of the through-hole (e.g., 114) of the dispensing body (e.g., 104).

The vapor channel 408 may be between the mouthpiece (e.g., 108) and the device compartment when the pod assembly 402 is inserted into the through-hole of the dispensing body.

An attachment structure (e.g., male/female member arrangement, magnetic arrangement) may be provided on at least one of the side walls (e.g., 116) of the through-hole (e.g., 114) and a side surface of the pod assembly 402. The attachment structure may be configured to engage and hold the pod assembly 402 upon insertion into the through-hole of the dispensing body. In addition, the channel outlet 412 may be utilized to secure the pod assembly 402 within the through-hole of the dispensing body. For instance, the dispensing body may be provided with a retractable vapor connector that is configured to insert into the channel outlet 412 so as to secure the pod assembly 402 while also supplementing the vapor path from the channel outlet 412 to the vapor passage (e.g., 106) of the dispensing body (e.g., 104). The vapor connector may also be a rounded structure and/or spring-loaded to facilitate its retraction (e.g., via spring compression) and protraction (e.g., via spring decompression).

In an example embodiment, the pre-vapor formulation compartment of the pod assembly 402 may surround the vapor channel 408. For instance, the vapor channel 408 may pass through a center of the pre-vapor formulation compartment, although example embodiments are not limited thereto.

Alternatively, instead of the vapor channel 408 shown in FIG. 19, a vapor channel may be in a form of a pathway that is arranged along at least one sidewall of the pre-vapor formulation compartment. For example, a vapor channel may be provided in a form of a pathway that spans between the first cap 404 and the second cap 14 while extending along one or both sides of an inner surface of the pod trim 410. As a result, the pathway may have a thin, rectangular cross-section, although example embodiments are not limited thereto. When the pathway is arranged along two sidewalls of the pre-vapor formulation compartment (e.g., both inner sidewalls of the pod trim 410), the pathway along each sidewall may be configured to converge at a position (e.g., channel outlet 412) that is aligned with the vapor passage (e.g., 106) of the dispensing body (e.g., 104) when the pod assembly 402 is received in the through-hole 114.

In another instance, the vapor channel may be in a form of a conduit that is arranged in at least one corner of the pre-vapor formulation compartment. Such a corner may be at the interface of the first cap 404 and/or the second cap 414 with the inner surface of the pod trim 410. As a result, the conduit may have a triangular cross-section, although example embodiments are not limited thereto. When the conduit is arranged in at least two corners (e.g., front corners, rear corners, diagonal corners, side corners) of the pre-vapor formulation compartment, the conduit in each corner may be configured to converge at a position (e.g., channel outlet 412) that is aligned with the vapor passage (e.g., 106) of the dispensing body (e.g., 104) when the pod assembly 402 is received in the through-hole 114.

The pre-vapor formulation compartment and the device compartment may be at opposite ends of the pod assembly 402. The device compartment may include a memory device. The memory device may be coded with an electronic identity to permit at least one of an authentication of the pod assembly 402 and a pairing of operating parameters specific to a type of the pod assembly 402 when the pod assembly 402 is inserted into the through-hole of the dispensing body (e.g., smart calibration). The electronic identity may help prevent counterfeiting. The operating parameters may help improve a vaping experience. In an example embodiment, the level of pre-vapor formulation in the pod assembly 402 may be tracked. Additionally, the activation of the pod assembly 402 may be restricted once its intended usage life has been exceeded. Thus, the pod assembly 402 (and 302) may be regarded as a smart pod.

A side surface of the pod assembly 402 includes at least one electrical contact 416 (e.g., two or three electrical contacts) and at least one electrical contact 417 (data connection) for data. The CC-NVM package or, alternatively, NVM is connected to the electrical contact 717 and one of the contacts 716. The dispensing body may be configured to perform at least one of supply power to and communicate with the pod assembly 402 via the at least one electrical contact 416. The at least one electrical contact 416 may be provided at an end of the pod assembly 402 corresponding to the device compartment. Because of its smart capability, the pod assembly 402 may communicate with dispensing body and/or another electronic device (e.g., smart phone). As a result, usage patterns and other information may be generated, stored, transferred, and/or displayed. Examples of the other information include, but are not limited to, vapor volume and a duration and/or count of instances of vapor drawing. As used in the present disclosure, the term "vapor drawing" refers to vapor being drawn through an outlet (e.g., vapor passage 106 or 206 and/or mouthpiece 108 or 208) of the e-vapor device (e.g., the e-vapor device 500 and/or an e-vapor device including dispensing body 104 or dispensing body 204). According to at least some example embodiments, an instance of vapor drawing begins when a negative pressure is applied to the outlet of the e-vapor device and ends when the application of the negative pressure ends. The smart capability, connecting features, and other related aspects of the pod assembly, dispensing body, and overall e-vapor apparatus are additionally discussed in U.S. Application No. 62/151,148 and U.S. Application No. 62/151,248, the entire contents of each of which are incorporated herein by reference.

Figure 20:
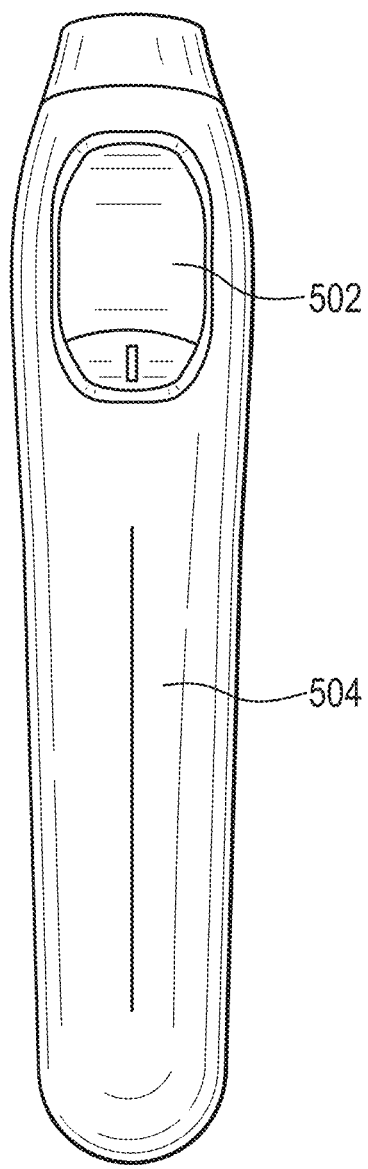
FIG. 20 is a view of an e-vapor apparatus with a pod assembly inserted in a dispensing body according to an example embodiment.

FIG. 20 is a view of an e-vapor apparatus with a pod assembly inserted in a dispensing body according to an example embodiment. Referring to FIG. 20, an e-vapor apparatus 500 includes a pod assembly 502 (e.g., smart pod) that is inserted within a dispensing body 504. The pod assembly 502 may be as previously described in connection with the pod assembly 302 and the pod assembly 402. As a result, the pod assembly 502 may be a hassle-free and leak-free element that can be replaced with relative ease when the pre-vapor formulation therein runs low/out or when another pod is desired.

Figure 21:
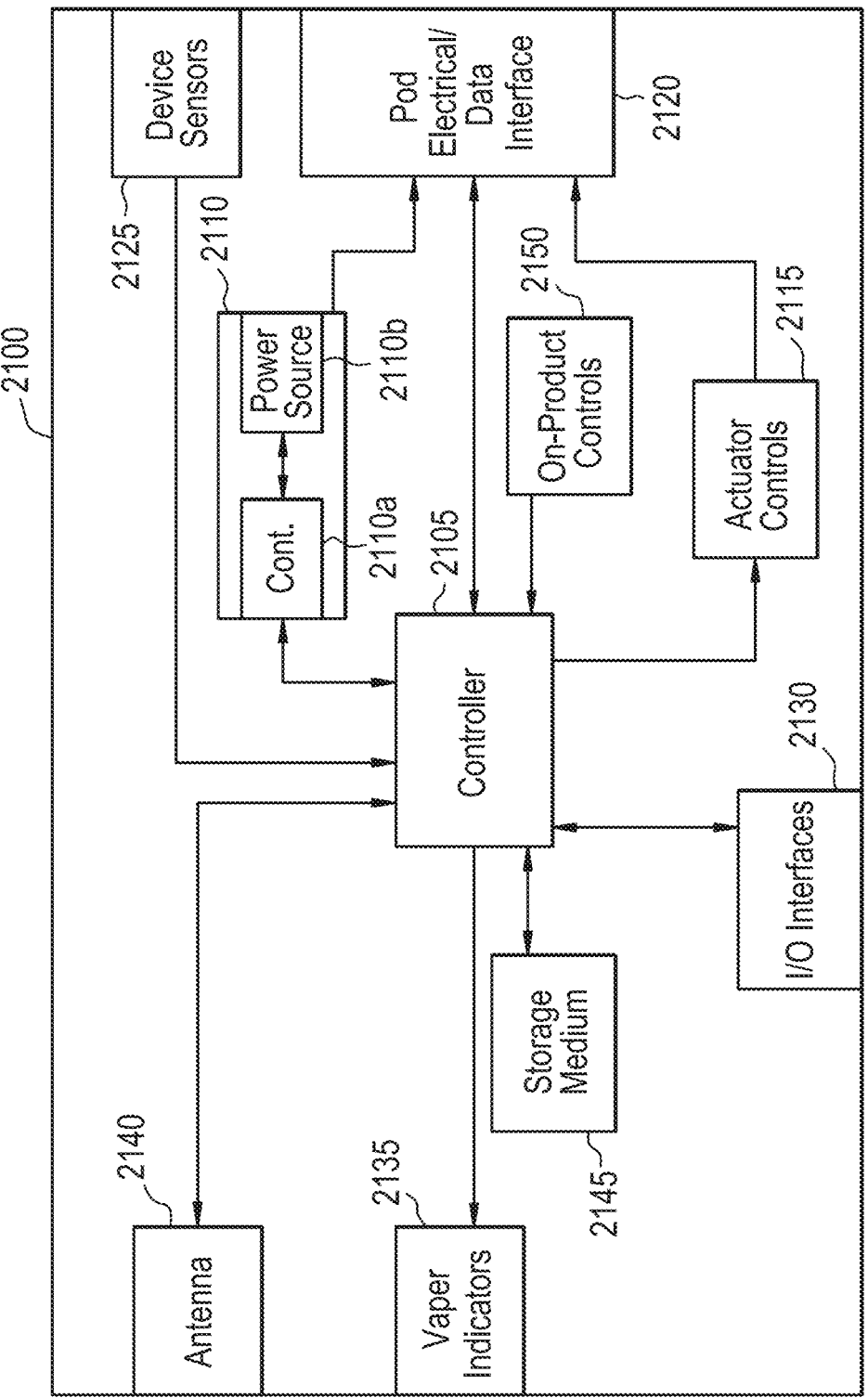
FIG. 21 illustrates a device system diagram of a dispensing body according to an example embodiment.

FIG. 21 illustrates a device system of a dispensing body according to an example embodiment. A device system 2100 may be the system within the dispensing body 104 and the dispensing body 204.

The device system 2100 includes a controller 2105, a power supply 2110, actuator controls 2115, a pod electrical/data interface 2120, device sensors 2125, input/output (I/O) interfaces 2130, vaper indicators 2135, at least one antenna 2140 and a storage medium 2145. The device system 2100 is not limited to the features shown in FIG. 21. For example, the device system 2100 may include additional elements. However, for the sake of brevity, the additional elements are not described. In other example embodiments, the device system 2100 may not include an antenna.

The controller 2105 may be hardware, firmware, hardware executing software or any combination thereof. When the controller 2105 is hardware, such existing hardware may include one or more Central Processing Units (CPUs), microprocessors, processor cores, multiprocessors, digital signal processors (DSPs), application-specific-integrated-circuits (ASICs), field programmable gate arrays (FPGAs) computers or the like configured as special purpose machines to perform the functions of the controller 2105. CPUs, microprocessors, processor cores, multiprocessors, DSPs, ASICs and FPGAs may generally be referred to as processing devices.

In the event where the controller 2105 is a processor executing software, the controller 2105 is configured as a special purpose machine (e.g., a processing device) to execute the software, stored in the storage medium 2145, to perform the functions of the controller 2105. The software may be embodied as program code including instructions for performing and/or controlling any or all operations described herein as being performed by the controller 2105.

As disclosed herein, the term "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Referring to FIG. 21, the controller 2105 communicates with the power supply 2110, the actuator control 2115, the pod electrical/data interface 2120, the device sensors 2125, the input/output (I/O) interfaces 2130, the vaper indicators 2135, the at least one antenna 2140.

The controller 2105 communicates with the CC-NVM or NVM in the pod through the pod electrical/data interface 2120. More specifically, the controller 2105 may utilize encryption to authenticate the pod. As will be described, the controller 2105 communicates with the CC-NVM package or NVM to authenticate the pod. More specifically, the non-volatile memory is encoded during manufacture with product and other information for authentication.

The memory device may be coded with an electronic identity to permit at least one of an authentication of the pod and a pairing of operating parameters specific to a type of the pod (or physical construction, such as a heating engine type) when the pod assembly 402 is inserted into the through-hole of the dispensing body. In addition to authenticating based on an electronic identity of the pod, the controller 2105 may authorize use of the pod based on an expiration date of the stored pre-vapor formulation and/or heater encoded into the NVM or the non-volatile memory of the CC-NVM. If the controller determines that the expiration date encoded into the non-volatile memory has passed, the controller may not authorize use of the pod and disable the e-vaping device.

The controller 2105 (or storage medium 2145) stores key material and proprietary algorithm software for the encryption. For example, encryption algorithms rely on the use of random numbers. The security of these algorithms depends on how truly random these numbers are. These numbers are usually pre-generated and coded into the processor or memory devices. Example embodiments may increase the randomness of the numbers used for the encryption by using the vapor drawing parameters e.g., durations of instances of vapor drawing, intervals between instances of vapor drawing, or combinations of them, to generate numbers that are more random and more varying from individual to individual than pre-generated random numbers. All communications between the controller 2105 and the pod may be encrypted.

Moreover, the pod can be used as a general pay-load carrier for other information such as software patches for the e-vaping device. Since encryption is used in all the communications between the pod and the controller 2105, such information is more secure and the e-vaping device is less prone to being installed with malwares or viruses. Use of the CC-NVM as an information carrier such as data and software updates allows the e-vaping device to be updated with software without it being connected to the Internet and for an adult vaper to go through a downloading process as with most other consumer electronics devices requiring periodic software updates.

The controller 2105 may also include a cryptographic accelerator to allow resources of the controller 2105 to perform functions other than the encoding and decoding involved with the authentication. The controller 2105 may also include other security features such as preventing unauthorized use of communication channels and preventing unauthorized access to data if a pod or adult vaper is not authenticated.

In addition to a cryptographic accelerator, the controller 2105 may include other hardware accelerators. For example, the controller 2105 may include a floating point unit (FPU), a separate DSP core, digital filters and Fast Fourier Transform (FFT) modules.

The controller 2105 is configured to operate a real time operating system (RTOS), control the system 2100 and may be updated through communicating with the NVM or CC-NVM or when the system 2100 is connected with other devices (e.g., a smart phone) through the I/O interfaces 2130 and/or the antenna 2140. The I/O interfaces 2130 and the antenna 2140 allow the system 2100 to connect to various external devices such as smart phones, tablets, and PCs. For example, the I/O interfaces 2130 may include a micro-USB connector. The micro-USB connector may be used by the system 2100 to charge the power source 2110b.

The controller 2105 may include on-board RAM and flash memory to store and execute code including analytics, diagnostics and software upgrades. As an alternative, the storage medium 2145 may store the code. Additionally, in another example embodiment, the storage medium 2145 may be on-board the controller 2105.

The controller 2105 may further include on-board clock, reset and power management modules to reduce an area covered by a PCB in the dispensing body.

The device sensors 2125 may include a number of sensor transducers that provide measurement information to the controller 2105. The device sensors 2125 may include a power supply temperature sensor, an external pod temperature sensor, a current sensor for the heater, power supply current sensor, air flow sensor and an accelerometer to monitor movement and orientation. The power supply temperature sensor and external pod temperature sensor may be a thermistor or thermocouple and the current sensor for the heater and power supply current sensor may be a resistive based sensor or another type of sensor configured to measure current. The air flow sensor may be a microelectromechanical system (MEMS) flow sensor or another type of sensor configured to measure air flow such as a hot-wire anemometer. As is noted above, the device sensors 2125 may include sensors, like an accelerometer, for monitoring movement and orientation as is shown in, for example, FIG. 23.

Figure 23:
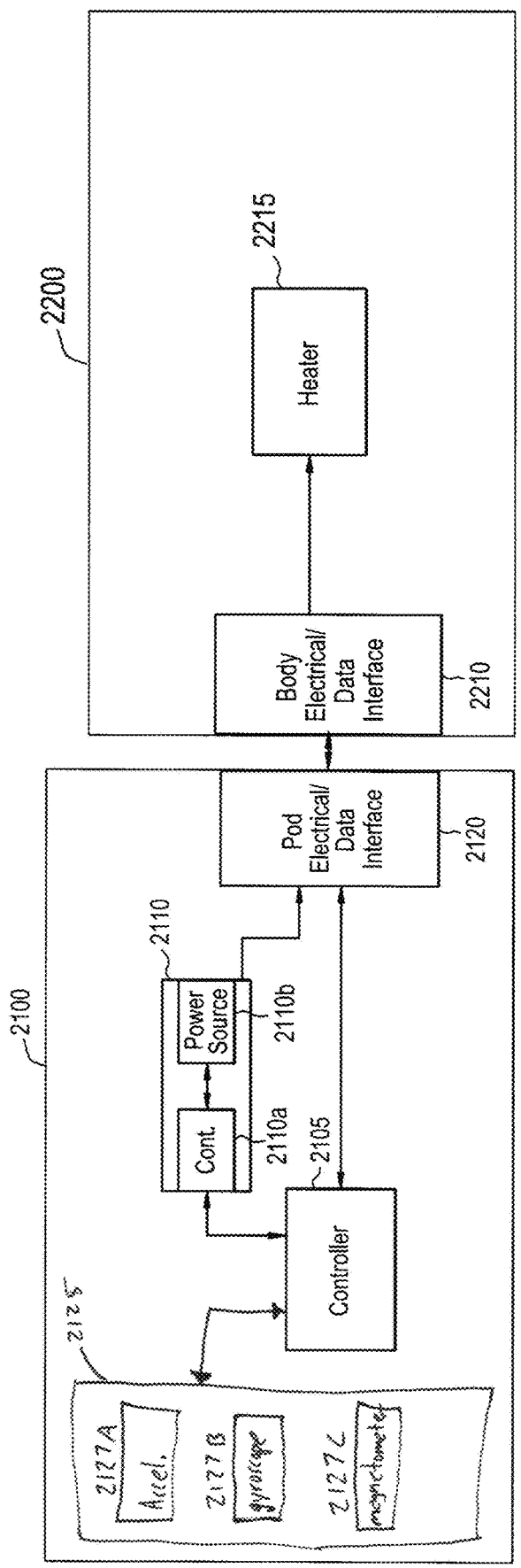
FIG. 23 illustrates a pod system connected to a device system according to an example embodiment.

FIG. 23 illustrates the pod system 2200 connected to the device system 2100 according to an example embodiment.

For example, the device sensors 2125 may include one or more accelerometers 2127A, one or more gyroscopes 2127B, and/or one or more magnetometers 2127C to monitor movement and orientation. For example, the device sensors 2125 may include at least one inertial measurement unit (IMU). The IMU may include, for example, 3-axis accelerometers, 3-axis-gyroscopes and 3-axis magnetometers. For example, the one or more accelerometers 2127A, one or more gyroscopes 2127B, and/or one or more magnetometers 2127C of FIG. 23 may be included in an IMU. Examples of an IMU included in the device sensors 2125 include, but are not limited to, the Invensense 10-axis MPU-9250 and the ST 9-axis STEVAL-MKI1119V1. As will be discussed in greater detail below with respect to FIGS. 24-25, the controller 2105 may use movement and/or orientation information detected by the device sensors 2125 to control a level of power output by the power supply 2110 to the heater 2215 through the pod electrical/data interface 2120 and the body electrical/data interface 2210.

The data generated from the number of sensor transducers may be sampled at a sample rate appropriate to the parameter being measured using a discrete, multi-channel analog-to-digital converter (ADC).

The controller 2105 may adapt heater profiles for a pre-vapor formulation and other profiles based on the measurement information received from the controller 2105. For the sake of convenience, these are generally referred to as vaping or vapor profiles.

The heater profile identifies the power profile to be supplied to the heater during the few seconds when vapor drawing takes place. For example, a heater profile can deliver maximum power to the heater when an instance of vapor drawing is initiated, but then after a second or so immediately reduce the power to half way or a quarter way.

The modulation of electrical power is usually implemented using pulse width modulation—instead of flipping an on/off switch where the power is either full on or off.

In addition, a heater profile can also be modified based on a negative pressure applied on the e-vaping device. The use of the MEMS flow sensor allows vapor drawing strength to be measured and used as feedback to the controller 2105 to adjust the power delivered to the heater of the pod, which may be referred to as heating or energy delivery.

When the controller 2105 recognizes the pod is currently installed (e.g., via SKU), the controller 2105 matches an associated heating profile that is designed for that particular pod. The controller 2105 and the storage medium 2145 will store data and algorithms that allow the generation of heating profiles for all SKUs. In another example embodiment, the controller 2105 may read the heating profile from the pod. The adult vapers may also adjust heating profiles to suit their preferences.

As shown in FIG. 21, the controller 2105 sends data to and receives data from the power supply 2110. The power supply 2110 includes a power source 2110b and a power controller 2110a to manage the power output by the power source 2110b.

The power source 2110b may be a Lithium-ion battery or one of its variants, for example a Lithium-ion polymer battery. Alternatively, the power source power source 2110b may be a Nickel-metal hydride battery, a Nickel cadmium battery, a Lithium-manganese battery, a Lithium-cobalt battery or a fuel cell. Alternatively, the power source 2110b may be rechargeable and include circuitry allowing the battery to be chargeable by an external charging device. In that case, the circuitry, when charged, provides power for a desired (or alternatively a pre-determined) number of instances of vapor drawing, after which the circuitry must be re-connected to an external charging device.

The power controller 2110a provides commands to the power source 2110b based on instructions from the controller 2105. For example, the power supply 2110 may receive a command from the controller 2105 to provide power to the pod (through the electrical/data interface 2120) when the pod is authenticated and the adult vaper activates the system 2100 (e.g., by activating a switch such as a toggle button, capacitive sensor, IR sensor). When the pod is not authenticated, the controller 2105 may either send no command to the power supply 2110 or send an instruction to the power supply 2110 to not provide power. In another example embodiment, the controller 2105 may disable all operations of the system 2100 if the pod is not authenticated.

In addition to supplying power to the pod, the power supply 2110 also supplies power to the controller 2105. Moreover, the power controller 2110a may provide feedback to the controller 2105 indicating performance of the power source 2110b.

The controller 2105 sends data to and receives data from the at least one antenna 2140. The at least one antenna 2140 may include a Near Field Communication (NFC) modem and a Bluetooth Low Energy (LE) modem and/or other modems for other wireless technologies (e.g., Wi-Fi). In an example embodiment, the communications stacks are in the modems, but the modems are controlled by the controller 2105. The Bluetooth LE modem is used for data and control communications with an application on an external device (e.g., smart phone). The NFC modem may be used for pairing of the e-vaping device to the application and retrieval of diagnostic information. Moreover, the Bluetooth LE modem may be used to provide location information (for an adult vaper to find the e-vaping device) or authentication during a purchase.

As described above, the system 2100 may generate and adjust various profiles for vaping. The controller 2105 uses the power supply 2110 and the actuator controls 2115 to regulate the profile for the adult vaper.

The actuator controls 2115 include passive and active actuators to regulate a desired vapor profile. For example, the dispensing body may include an inlet channel within a mouthpiece. The actuator controls 2115 may control the inlet channel based on commands from the controller 2105 associated with the desired vapor profile.

Moreover, the actuator controls 2115 are used to energize the heater in conjunction with the power supply 2110. More specifically, the actuator controls 2115 are configured to generate a drive waveform associated with the desired vaping profile. As described above, each possible profile is associated with a drive waveform. Upon receiving a command from the controller 2105 indicating the desired vaping profile, the actuator controls 2115 may produce the associated modulating waveform for the power supply 2110.

The controller 2105 supplies information to the vaper indicators 2135 to indicate statuses and occurring operations to the adult vaper. The vaper indicators 2135 include a power indicator (e.g., LED) that may be activated when the controller 2105 senses a button pressed by the adult vaper. The vaper indicators 2135 may also include a vibrator, speaker, an indicator for current state of an adult vaper-controlled vaping parameter (e.g., vapor volume) and other feedback mechanisms.

Furthermore, the system 2100 may include a number of on-product controls 2150 that provide commands from an adult vaper to the controller 2105. The on-product controls 2150 include an on-off button which may be a toggle button, capacitive sensor or IR sensor, for example. The on-product controls 2150 may further include a vaping control button (if the adult vaper desires to override the buttonless vaping feature to energize the heater), a hard reset button, a touch based slider control (for controlling setting of a vaping parameter such as vapor drawing volume), a vaping control button to activate the slider control and a mechanical adjustment for an air inlet. Hand to mouth gesture (HMG) detection is another example of buttonless vaping and will be discussed in greater detail below with reference to FIG. 24.

Once a pod is authenticated, the controller 2105 operates the power supply 2110, the actuator controls 2115, vaper indicators 2135 and antenna 2140 in accordance with the adult vaper using the e-vaping device and the information stored by the NVM or CC-NVM on the pod. Moreover, the controller 2105 may include logging functions and be able to implement algorithms to calibrate the e-vaping device. The logging functions are executed by the controller 2105 to record usage data as well any unexpected events or faults. The recorded usage data may be used for diagnostics and analytics. The controller 2105 may calibrate the e-vaping device using buttonless vaping (i.e., vaping without pressing a button such as generating a vapor when a negative pressure is applied on the mouthpiece), an adult vaper configuration and the stored information on the CC-NVM or NVM including vapor drawing sensing, pre-vapor formulation level and pre-vapor formulation composition. For example, the controller 2105 may command the power supply 2110 to supply power to the heater in the pod based on a vaping profile associated with the pre-vapor formulation composition in the pod. Alternatively, a vaping profile may be encoded in the CC-NVM or NVM and utilized by the controller 2105.

Figure 22A:
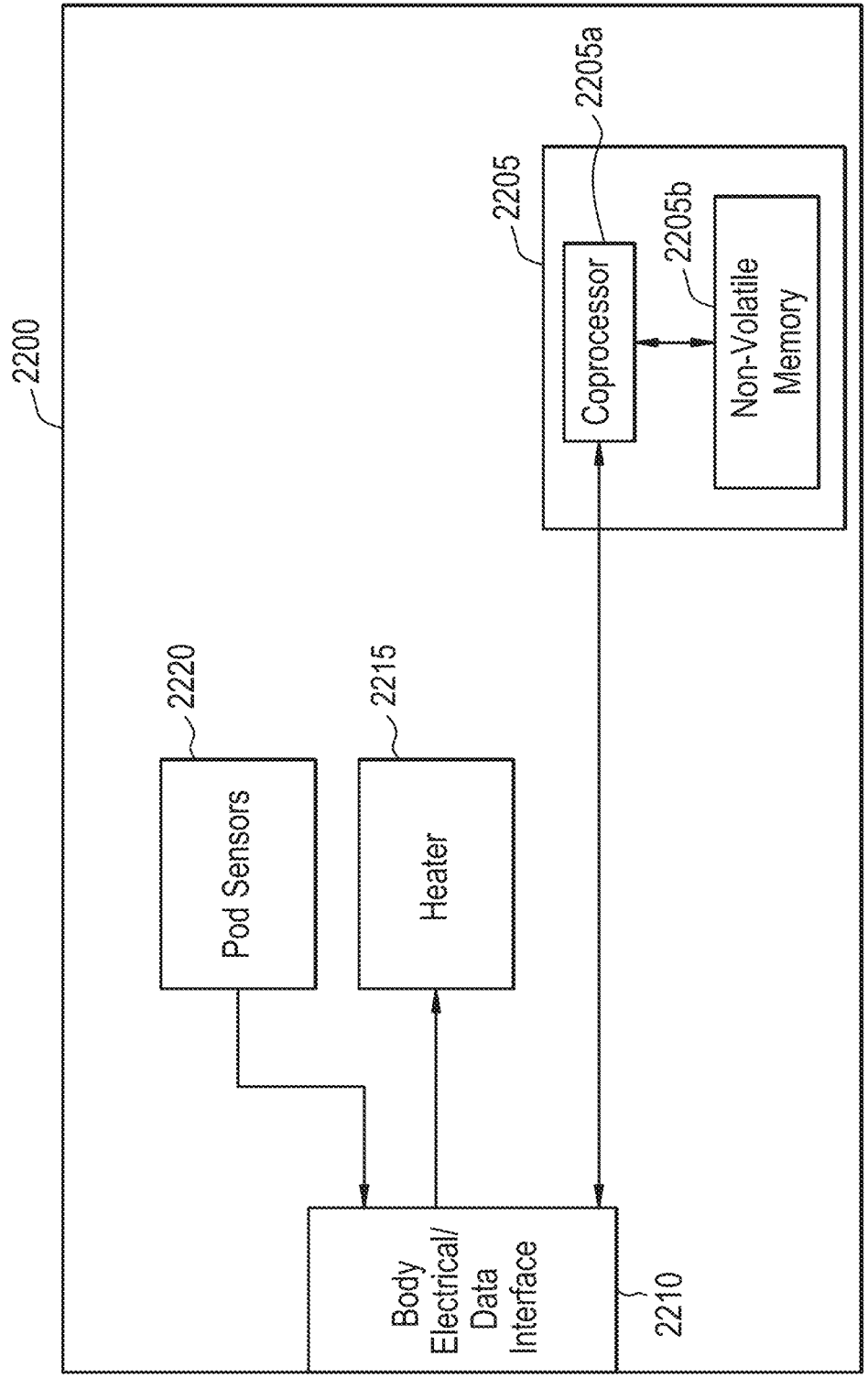
FIG. 22A illustrates a pod system diagram of a dispensing body according to an example embodiment.

FIG. 22A illustrates a pod system diagram of a dispensing body according to an example embodiment. A pod system 2200 may be within the pod assembly 502, the pod assembly 302 and the pod assembly 402.

As shown in FIG. 22A, the pod system 2200 includes a CC-NVM 2205, a body electrical/data interface 2210, a heater 2215 and pod sensors 2220. The pod system 2200 communicates with the device system 2100 through the body electrical/data interface 2210 and the pod electrical/data interface 2120. The body electrical/data interface 2210 may correspond to the battery contacts 416 and data connection 417 connected within the pod assembly 402, shown in FIG. 19, for example. Thus, the CC-NVM 2205 is coupled to the data connection 417 and the battery contacts 416.

The CC-NVM 2205 includes a cryptographic coprocessor 2205a and a non-volatile memory 2205b. The controller 2105 may access the information stored on the non-volatile memory 2205b for the purposes of authentication and operating the pod by communicating with the cryptographic coprocessor 2205a.

In another example embodiment, the pod may not have a crytopgraphic coprocessor. For example, FIG. 22B illustrates an example of the pod system of FIG. 22A in which the cryptographic coprocessor 2205a is omitted, according to an example embodiment. As is shown in FIG. 22B, the pod system 2200 may include the non-volatile memory 2205b in place of the CC-NVM 2205, and the cryptographic coprocessor 2205a is omitted. When no cryptographic coprocessor exists in the pod system 2200, the controller 2105 may read data from the non-volatile memory 2205b without use of the cryptographic coprocessor to control/define the heating profile.

The non-volatile memory 2205b may be coded with an electronic identity to permit at least one of an authentication of the pod and a pairing of operating parameters specific to a type of the pod when the pod assembly is inserted into the through-hole of the dispensing body. In addition to authenticating based on an electronic identity of the pod, the controller 2105 may authorize use of the pod based on an expiration date of the stored pre-vapor formulation and/or heater encoded into the non-volatile memory 2205b. If the controller determines that the expiration date encoded into the non-volatile memory non-volatile memory 2205b has passed, the controller may not authorize use of the pod and disable the e-vaping device.

Moreover, the non-volatile memory 2205b may store information such as a stock keeping unit (SKU) of the pre-vapor formulation in the pre-vapor formulation compartment (including pre-vapor formulation composition), software patches for the system 2100, product usage information such as vapor drawing instance count, vapor drawing instance duration, and pre-vapor formulation level. The non-volatile memory 2205b may store operating parameters specific to the type of the pod and the pre-vapor formulation composition. For example, the non-volatile memory 2205b may store the electrical and mechanical design of the pod for use by the controller 2105 to determine commands corresponding to a desired vaping profile.

The pre-vapor formulation level in the pod may be determined in one of two ways, for example. In one example embodiment, one of the pod sensors 2220 directly measures the pre-vapor formulation level in the pod.

In another example embodiment, the non-volatile memory 2205b stores the vapor drawing instance count from the pod and the controller 2105 uses the vapor drawing instance count as a proxy to the amount of pre-vapor formulation vaporized.

The controller 2105 and/or the storage medium 2145 may store pre-vapor formulation calibration data that identifies an operating point for the pre-vapor formulation composition. The pre-vapor formulation calibration data include data describing how flow rate changes with a remaining pre-vapor formulation level or how volatility changes with an age of the pre-vapor formulation and may be used for calibration by the controller 2105. The pre-vapor formulation calibration data may be stored by the controller 2105 and/or the storage medium 2145 in a table format. The pre-vapor formulation calibration data allows the controller 2105 to equate the vapor drawing instance count to the amount of pre-vapor formulation vaporized.

The controller 2105 writes the pre-vapor formulation level and vapor drawing instance count back to the non-volatile memory 2205b in the pod so if the pod is removed from the dispensing body and later on re-installed, an accurate pre-vapor formulation level of the pod will still be known by the controller 2105.

The operating parameters (e.g., power supply, power duration, air channel control) are referred to as a vaping profile. Moreover, the non-volatile memory 2205b may record information communicated by the controller 2105. The non-volatile memory 2205b may retain the recorded information even when the dispensing body becomes disconnected from the pod.

In an example embodiment, the non-volatile memory 2205b may be a programmable read only memory.

The heater 2215 is actuated by the controller 2105 and transfers heat to at least a portion of the pre-vapor formulation in accordance with the commanded profile (volume, temperature (based on power profile) and flavor) from the controller 2105.

The heater 2215 may be a planar body, a ceramic body, a single wire, a cage of resistive wire, a wire coil surrounding a wick, a mesh, a surface or any other suitable form for example. Examples of suitable electrically resistive materials include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater may be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. In one embodiment, the heater 14 comprises at least one material selected from the group consisting of stainless steel, copper, copper alloys, nickel-chromium alloys, superalloys and combinations thereof. In an embodiment, the heater 2215 is formed of nickel-chromium alloys or iron-chromium alloys. In one embodiment, the heater 2215 can be a ceramic heater having an electrically resistive layer on an outside surface thereof.

In another embodiment, the heater 2215 may be constructed of an iron-aluminide (e.g., FeAl or Fe.sub.3Al), such as those described in commonly owned U.S. Pat. No. 5,595,706 to Sikka et al. filed Dec. 29, 1994, or nickel aluminides (e.g., Ni.sub.3Al), the entire contents of which are hereby incorporate by reference.

The heater 2215 may determine an amount of pre-vapor formulation to heat based on feedback from the pod sensors or the controller 2105. The flow of pre-vapor formulation may be regulated by a micro-capillary or wicking action. Moreover, the controller 2105 may send commands to the heater 2215 to adjust an air inlet to the heater 2215.

The pod sensor 2220 may include a heater temperature sensor, pre-vapor formulation flow rate monitor and air flow monitor. The heater temperature sensor may be a thermistor or thermocouple and the flow rate sensing may be performed by the system 2200 using electrostatic interference or an in-pre-vapor formulation rotator. The air flow sensor may be a microelectromechanical system (MEMS) flow sensor or another type of sensor configured to measure air flow.

The data generated from the pod sensors 2220 may be sampled at a sample rate appropriate to the parameter being measured using a discrete, multi-channel analog-to-digital converter (ADC).

According to at least some example embodiments, the controller 2105 may also control the heater 2215 in response to detecting a hand to mouth gesture (HMG). As is noted above, with reference to FIG. 21, an e-vapor device according to at least some example embodiments may implement a buttonless vaping feature. As an example of a buttonless vaping feature, the controller 2105 may determine when an adult vaper makes a hand to mouth gesture (HMG) based on measurements from device sensors 2125. An HMG is a gesture in which an adult vaper's hand moves towards the adult vaper's mouth. An HMG made with respect to an e-vapor device (e.g., the e-vapor device 500 and/or an e-vapor device including dispensing body 104 or dispensing body 204) may indicate that vapor drawing will begin soon. According to at least some example embodiments, the controller 2105 may control a state and/or operation mode of the e-vapor device or one or more elements thereof based on the detection of an HMG. For example, as is discussed in greater detail below with reference to Equations 8 and 9, the controller 2105 may control a state and/or operation mode of the heater 2215 by detecting an HMG based on the output of a classifier. The heater 2215 may also be referred to herein as the heating engine 2215 or heater engine 2215.

Figure 24:
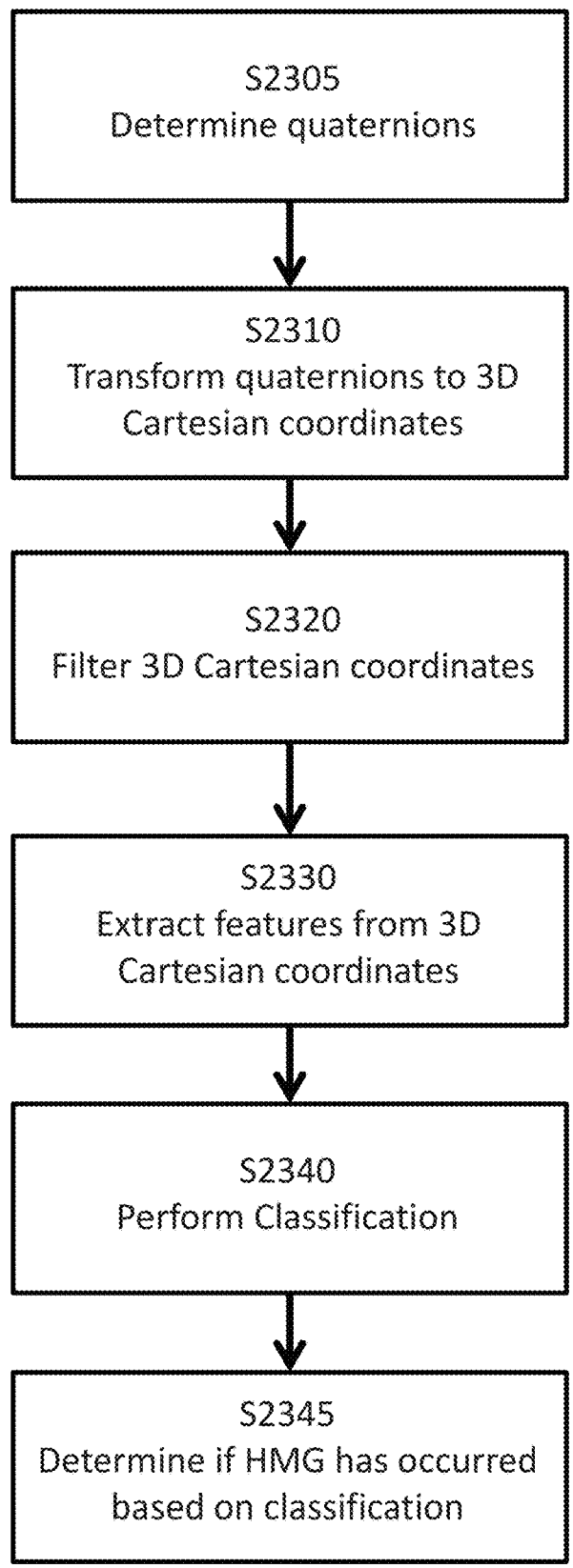
FIG. 24 illustrates an example algorithm for performing hand to mouth gesture (HMG) detection.

FIG. 24 illustrates an example algorithm for performing hand to mouth gesture HMG detection. According to at least some example embodiments, the HMG detection algorithm of FIG. 24 is performed by the controller 2105 of system 2100, which may be included in an e-vapor device (e.g., the e-vapor device 500 and/or an e-vapor device including dispensing body 104 or dispensing body 204). Referring to FIG. 24, the HMG detection algorithm may use movement and/or orientation measurements detected by device sensors 2125.

In operation S2305, quaternions are determined based on movements of an e-vapor device. For example, as is noted above with reference FIG. 21, the device sensors 2125 may include at least one IMU. As an example, the IMU may output movement and/or orientation measurements to the controller 2105 in the form of quaternions. As another example, the IMU may output movement and/or orientation measurements to the controller 2105 in the form of accelerometer measurements, gyroscope measurements, and/or magnetometer measurements, and quaternions may be determined by the controller 2105 based on the accelerometer measurements, gyroscope measurements, and/or magnetometer measurements. According to at least some example embodiments, the quaternions received by, or determined by, the controller 2105 may be unit quaternions. The quaternions may be received by, or determined by, the controller 2105, for example, every 20 ms thus resulting in an update rate (or frequency) of 50 Hz. According to at least some example embodiments, the quaternions received by, or determined by, the controller 2105 may be stored by the controller 2105 in memory (e.g., storage medium 2145) such that historical quaternions are available for use by the HMG detection algorithm as will be discussed in greater detail below.

The generation of quaternions in operation S2305 will now be discussed in greater detail. For example, according to at least some example embodiments, at a resting position, an E-vapor device is assumed to be located at a reference point $r_0 = 1j$. The reference point $r_0$ is a unit vector representing the tip of a forearm (elbow to hand) of unit length. This reference point $r_0$ can also be regarded as point (0,1,0) in a 3D Cartesian (x,y,z) space.

According to at least some example embodiments, a positional sensor of the E-vapor device (e.g., one or more of the device sensors 2125) sends out 4 real numbers ($q_0, q_1, q_2, q_3$) every 20 ms as the e-vapor device moves in space. At any time t, data from the positional sensor can be denoted by a quaternion q(t) defined by Equation 1 or Equation 2, which is an alternate expression of Equation 1:

$$q[t]q_0[t] + q_1[t]i + q_2[t]j + q_3[t]k; \qquad \text{Equation 1}$$

$$q = q_0 + q_1 i + q_2 j + q_3 k \text{ or } q = q_0(\text{scalar}) + q(\text{vector}). \qquad \text{Equation 2}$$

As is known with respect to quaternions, in Equations 1 and 2, 1, j and k are related such that $i^2 = j^2 = k^2 = -1$, and $ij = k = -ji$.

In operation S2310, the quaternions are transformed into Cartesian coordinates. For example, in operation S2310, the controller 2105 may transform the quaternions into 3-dimensional Cartesian coordinates. For example, the stream of quaternions generated in operation S2305 indicates the successive rotations (i.e., changes of positions), relative to the reference point $r_0$, of the e-vapor device as the e-vapor device moves in space. Starting with the reference point (resting position), each quaternion allows a new position of the e-vapor device r to be computed in accordance with Equation 3:

$$r = q r_0 q^* = (q_0^2 - \|q\|^2) r_0 + 2(q \cdot r_0) q + 2 q_0 (q \times r_0), \quad \text{Equation 3}$$

where q* is the complex conjugate of q, defined as $q^* = q_0 - q_1 i - q_2 j - q_3 k$, and reference point $r_0 = 1j$, as is noted above. Like Equation 2, the time reference (i.e., [t]) is dropped from Equation 3 for ease of description.

Since $r_0$ is a vector, the above quaternion mathematical operation described by Equation 3 will yield r as a vector also. As a vector, r describes the new position of the e-vapor device in a 3D Cartesian space. Accordingly, in operation S2310 a transformation from reference point vector $r_0$ to vector r, is repeated over time t to generate new values for vector r (i.e., r[t]), thus defining corresponding x, y, z Cartesian coordinates of new positions of the e-vapor device at times t (i.e., vectors r and r[t] are each three-element vectors that include, as elements, coordinates x, y, and z).

Thus, in accordance with Equations 1-3, the controller 2105 may transform quaternions (e.g., q or q[t]) generated based on measurements of the device sensors 2125 into 3-D Cartesian coordinates (e.g., r or r[t]). After operation S2310, the HMG detection algorithm proceeds to operation S2320.

In operation S2320, the 3-D Cartesian coordinates determined in operation S2310 are filtered by the controller 2105 to generate filtered 3-D Cartesian coordinates. The filtering performed in operation S2320 may improve the accuracy of the features extracted in operation S2330, for example, by improving the signal-to-noise ratio of the features extracted in operation S2330. A filter used in operation S2320 may be, for example, a low-pass filter. A filter used in operation S2320 may be, for example, a finite impulse response filter (FIR) or an infinite impulse response (IIR) filter. Examples of a type of filter that may be used in operation S2320 include, but are not limited to, a $20^{th}$ order FIR filter, a $10^{th}$ order FIR filter, a $10^{th}$ order IIR filter, and a $5^{th}$ order IIR filter. According to at least some example embodiments, the filtering performed in operation S2320 may be configured to reduce or remove high frequency noise that, if not removed, may introduce noise to linear speed v[t] calculations, which will be discussed in greater detail below with respect to the feature extraction operation S2330. According to at least some example embodiments, the filtering performed in operation S2320 may be configured to remove motion artifacts corresponding to motion data representing non-HMG motions like, for example, walking (i.e., walking when no HMG is being performed).

Figure 25:
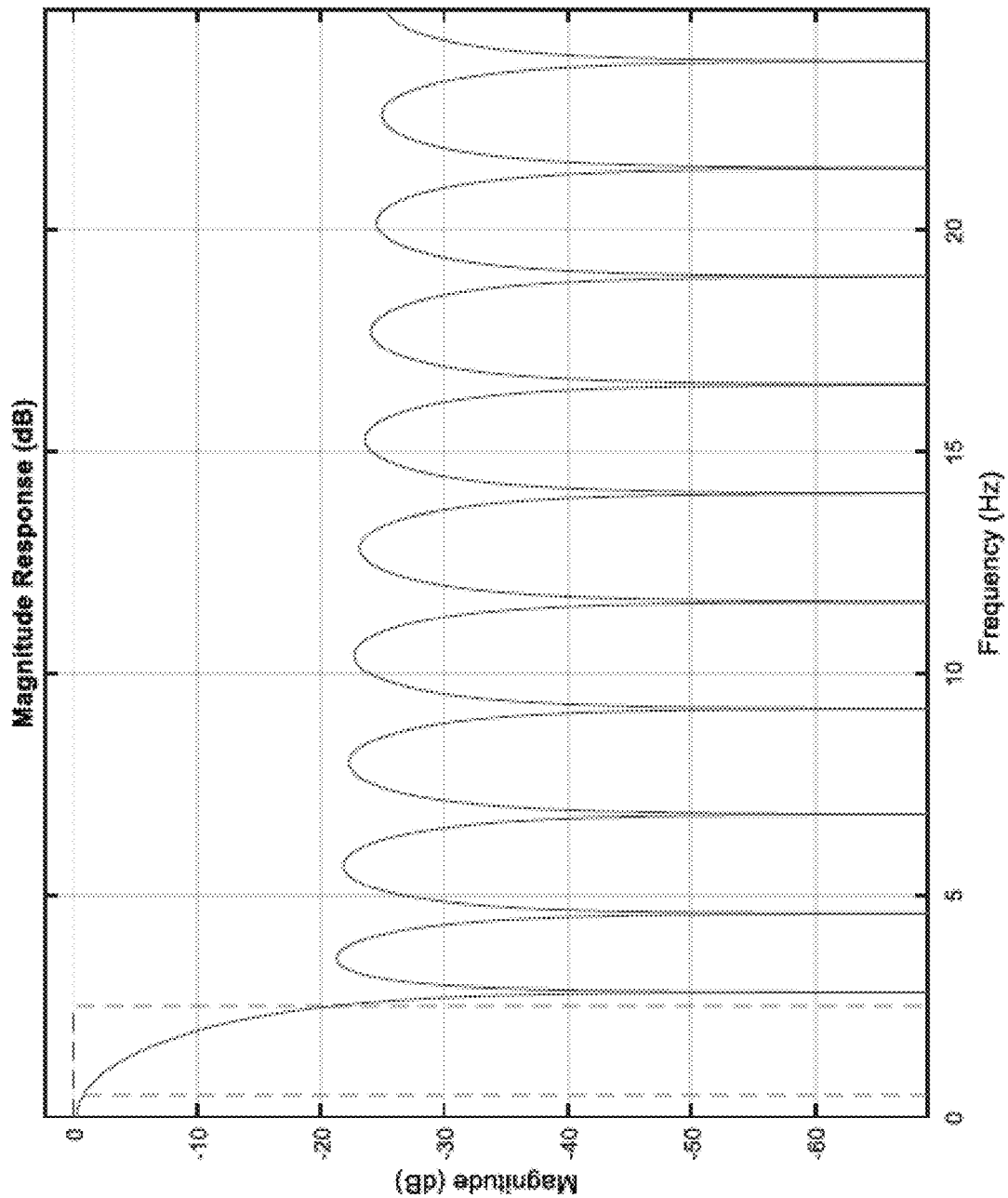
FIG. 25 illustrates a plot of a frequency response corresponding to filtering performed in accordance with Equation 4.

For example, a 3-D Cartesian coordinate determined in operation S2310 may be filtered by applying Equation 4, $$f[t] = \sum_{n=1}^{N} b[n] r[t - n], \quad \text{Equation 4}$$

to each dimension of the 3-D Cartesian coordinate. FIG. 25 illustrates a plot of a frequency response corresponding to filtering performed in accordance with Equation 4. Referring to Equation 4, r[t−n] is a three element vector that includes, as the three elements, the unfiltered values of an x, y and z coordinate at time t-n. Further, f[t] is a three element vector that includes, as the three elements, the filtered values of the x, y and z coordinates at time t. Additionally, b[n] is a constant coefficient pertaining to the filter chosen. For the purpose of clarity, operation S2320 will be described with reference to an example in which the controller 2105 performs filtering of the 3-D Cartesian coordinates determined in operation S2310 using an order 20 FIR filter. With respect to the above referenced example, the value of N in Equation 4 may be equal to 20, and constant coefficient b[n] may be defined by Table 1 below.

TABLE 1

| Coefficient | Value | Coefficient | Value |
| --- | --- | --- | --- |
| b[1] | 0.044563075892158709 | b[21] | 0.044563075892158709 |
| b[2] | 0.031036021853680543 | b[20] | 0.031036021853680543 |
| b[3] | 0.031409596396058503 | b[19] | 0.031409596396058503 |
| b[4] | 0.037277883907421094 | b[18] | 0.037277883907421094 |
| b[5] | 0.04193728641405934 | b[17] | 0.04193728641405934 |
| b[6] | 0.046982842619960649 | b[16] | 0.046982842619960649 |
| b[7] | 0.050974200999071843 | b[15] | 0.050974200999071843 |
| b[8] | 0.054610952216487221 | b[14] | 0.054610952216487221 |
| b[9] | 0.056998917285984399 | b[13] | 0.056998917285984399 |
| b[10] | 0.058730364996784766 | b[12] | 0.058730364996784766 |
| b[11] | 0.059173996065795362 | | |

FIG. 25 illustrates a plot of a frequency response corresponding to filtering performed in accordance with Equation 4. According to at least some example embodiments, the order 20 FIR filter used in operation S2320 may have the following attributes:

2 Hz passband frequency,
2.5 Hz stopband frequency, and
Stopband decay of 5 dBm/decade.

While, for the purpose of clarity, the HMG detection algorithm of FIG. 24 is described primarily with respect to a scenario in which the controller 2105 performs the filtering operation S2320 on 3-D Cartesian coordinates after performing the transformation operation S2310, at least some example embodiments are not limited to this scenario. For example, as an alternative, according to at least some example embodiments, the controller 2105 may perform the HMG detection algorithm illustrated in FIG. 24 by omitting the filtering operation S2320 such that the 3-D Cartesian coordinates used by the controller 2105 in the feature detection operation S2330 are the unfiltered 3-D Cartesian coordinates determined in the transformation operation S2310. As another alternative, according to at least some example embodiments, the controller 2105 may perform the filtering operation S2320 before performing the transformation operation S2310. For example, the controller 2105 may perform a filtering operation directly on the quaternions received by, or determined by, the controller 2105 to generate filtered quaternions. After performing the filtering operation, the controller 2105 may transform the filtered quaternions into 3-D Cartesian coordinates using, for example, Equations 1-3 discussed above, such that the 3-D Cartesian coordinates used by the controller 2105 in the feature detection operation S2330 are the 3-D Cartesian coordinates that were transformed from the filtered quaternions.

Returning to FIG. 24, in operation S2330, features are extracted from the 3-D Cartesian coordinates. The features extracted from the 3-D Cartesian coordinates (which may also be referred to herein as "movement features") are features related to the movement and/or orientation of the e-vapor device, where the 3-D Cartesian coordinates are provided as the 3-element vector r as defined above with reference to Equations 1-3. For example, in operation S2330, the controller 2105 may extract the following movement features from the 3-D Cartesian coordinates determined from operations S2310 or operations S2310 and S2320: distance from rest point location d[t] and linear speed v[t]. The distance from rest point location feature d[t] refers to a distance between a point r[t] and a rest point $r_{rest}$ at time t, where the point r[t] is a location (i.e., a point in 3-D space) of the e-vapor device at time t, and the rest point $r_{rest}$ is a location (i.e., a point in 3-D space) at which the e-vapor device last rested, where resting refers to a movement state of the e-vapor device in which the e-vapor device is stationary or substantially stationary as will be discussed in greater detail below with reference to Expression 6.

As is noted above, the quaternions (i.e., q[t]) may be sampled by (i.e., received by, or determined by) the controller 2105, for example, every 20 ms. Accordingly, point r[t] may be updated every 20 ms, thus resulting in an update rate (or frequency) of 50 Hz. Consequently, according to at least some example embodiments, the controller 2105 may determine 3-D Cartesian coordinates corresponding to the quaternions at or near a rate (or frequency) of 50 Hz. Thus, a linear speed of the e-vapor device at time t, v[t], may be determined based on locations of the e-vapor device at time t and t−1 in accordance with Equation 5:

$$v[t]=\|r[t]-r[t-1]\| \text{ meters per sample.} \quad \text{Equation 5}$$

In Equation 5, linear speed v[t] is expressed in units of meters per sample. Linear speed v[t] may also be expressed as $v[t]=\|r[t]-r[t-1]\|/\Delta t$ meters per second (m/s), where $\Delta t$ may be expressed as [1/sample frequency]. For example, the linear speed v[t] of the e-vapor device at time t in units of m/s may be expressed as $v[t]=\|r[t]-r[t-1]\|/[\frac{1}{50}]$, when a quaternion sample rate is 50 Hz.

Further, the rest point $r_{rest}$ may be defined as a latest location for which the e-vapor device is determined (e.g., by the controller 2105) to be stationary or substantially stationary by satisfying the requirements expressed in Expression 6:

$$r[t]=r_{rest} \text{ if } v[t]<V_{threshold} \wedge v[t-1]<V_{threshold} \wedge v[t-2]<V_{threshold}, \quad \text{Expression 6}$$

where $V_{threshold}$ is a speed threshold value. Example values for $V_{threshold}$ with respect to a sample rate (or frequency) of 50 Hz include, but are not limited to, 0.025 m per sample and 0.5 m per sample.

Further, the distance from rest point at time t, d[t], may be defined based on point r[t] and rest point $r_{rest}$ in accordance with Equation 7:

$$d[t]=\|r[t]-r_{rest}\|. \quad \text{Equation 7}$$

Thus, in operation S2330, the controller 2105 may extract movement features with respect to a time t including the distance from rest point location d[t] and the linear speed v[t] using, for example, Equations 5 and 7 and Expression 6. After operation S2330, the HMG determination algorithm proceeds to operation S2340.

In operation S2340, the controller 2105 determines whether or not an HMG has occurred with respect to the e-vapor device based on the movement features extracted in operation S2330.

For example, the controller 2105 may use one or more machine learning-based techniques for determining whether or not an HMG has occurred with respect to the e-vapor device. For example, the controller 2105 may utilize a neural network to determine, based on the movement features extracted in operation S2330, whether or not an HMG has occurred with respect to the e-vapor device. As another example, the controller 2105 may use linear discriminant analysis (LDA) for determining whether or not an HMG has occurred using. LDA-based techniques for determining whether or not an HMG has occurred will be discussed in greater detail below.

According to at least some example embodiments, in operation S2340, the controller 2105 uses a classifier to determine whether or not an HMG has occurred. According to at least some example embodiments, the controller 2105 may use, as inputs to the classifier, the distance from rest point location feature d[t], and the linear speed feature v[t], in order to determine, based on an output of the classifier, whether or not an HMG occurred at or near time t. Consequently, through use of the classifier, the controller 2105 is configured to distinguish between HMG movements and non-HMG movements.

The classifier used by the controller 2105 in operation S2340 may be referred to an HMG classifier. According to at least some example embodiments, the HMG classifier may be a classifier generated based on training data using linear discriminant analysis (LDA). A classifier generated based on training data using LDA may also be referred to herein as a "LDA classifier." According to at least some example embodiments, the training data used to generate the HMG classifier may be collected during a training process by observing a plurality of known motion states including known HMGs (i.e., motions states that are known to be HMGs) and known non-HMGs (i.e., motions states that are not to be HMGs), and recording movement features (e.g., the distance from rest point location feature, d[t], and the linear speed feature, v[t]) associated with the observed known motion states. LDA may then be applied to the collected data to generate the HMG classifier. According to at least some example embodiments, the HMG classifier used by the controller 2105 in operation S2340 may be initially generated during the above-reference training process, and the above-reference training process may be performed by, for example, a computer system outside the e-vapor device. After initial generation, the HMG classifier may be embodied in the e-vapor device in the form of circuitry, for example circuitry included in the controller 2105 that is structurally designed to embody the behavior of the HMG classifier by detecting HMG based on input movement features in the manner defined by the generated HMG classifier. Alternatively, the HMG classifier may be embodied in the e-vapor device in the form of a program and/or program instructions that may be stored in the storage medium 2145 and executed by a processor included in the e-vapor device such that the processor (e.g., the controller 2105) detects HMG based on input movement features in the manner defined by the generated HMG classifier. As another alternative, the HMG classifier may be embodied in the e-vapor device in the form of a combination of the above-referenced circuitry and processor executing program instructions. An example of the above-referenced HMG classifier will now be discussed in greater detail below.

An example of the HMG classifier which the controller 2105 may use to detect the occurrence of a HMG is provided by the LDA model defined below with reference to Equation 8:

$$\eta = \sum_{m=1}^{M} c[m]\phi[m], \quad \text{Equation 8}$$

where φ[m] is a feature φ corresponding index m, c[m] is a coefficient c corresponding to index m, M=3, and η is a classifier output. Example values for feature φ[m] and model coefficients c[m] are defined by Table 2 below. As is shown below, feature Φ[1] and model coefficients c[1], c[2] and c[3] may each be constants.

TABLE 2

| Feature, Φ[m] | Value | Model Coefficient, c[m] | Value |
|---|---|---|---|
| Φ[1] | Constant offset | c[1] | 5.2523 |
| Φ[2] | distance from rest point location d[t] in meters (m) | c[2] | −129.4848 |
| Φ[3] | linear speed v[t] in meters per second (m/s) | c[3] | −13.160 |

According to at least some example embodiments, the constant offset feature for all times t is 1 (i.e., Φ [1]=1, for all times t), and Equation 8 may be simplified in the manner shown below with respect to Equation 9:

$$\eta = c[1] + \sum_{m=2}^{M} c[m]\phi[m].  \quad \text{Equation 9}$$

Referring to Equations 8 and 9, the summation of the product of operands c[m] and φ[m] over indexes m=1, 2, 3 is calculated as classifier output η. Thus, in operation S2340, the controller 2105 may perform a classification operation by generating classifier output η in the manner discussed above with reference to Equations 8 and 9.

In operation S2345, the controller 2105 may determine whether or not an HMG has occurred based on the result of the classification operation performed in operation S2340. According to at least some example embodiments, for a time t, the controller 2015 determines that HMG has occurred when classifier output η is greater than 0 and determines that HMG has not occurred (i.e., no movement occurred or movement other than HMG occurred) when classifier output q is less than or equal to 0, as is shown below in Table 3.

TABLE 3

| Model Output | Classification |
|---|---|
| η > 0 | HMG |
| η ≤ 0 | Other |

Thus, in operation S2345, the controller 2105 may determine whether or not a HMG occurred with respect to a time t based on a result of Equations 8 or Equation 9. Further, in operation S2345 the controller 2015 may output a state decision based on the determination of whether or not an HMG occurred.

For example, the controller 2105 may control an operation mode of the heater engine 2215 to change between a plurality of states, in response to detecting an HMG. For example, the controller 2105 may implement a preheating operation as is described in greater detail below.

According to at least one example embodiment, an operation mode of the heater engine 2215 may have one of three states: OFF, PREHEAT and ON. According to at least some example embodiments, the OFF state is a state in which a relatively low amount of power or, alternatively, no power is supplied to the heater engine 2215 by the e-vapor device; the PREHEAT state is a state in which an amount of power supplied to the heater engine 2215 by the e-vapor device is higher than the amount of power supplied in the OFF state; and the ON state is a state in which an amount of power supplied to the heater engine 2215 by the e-vapor device is higher than the amount of power supplied in the PREHEAT state. According to at least one example embodiment, in operation S2345, the controller 2105 may perform a preheating operation by controlling the heater engine 2215 to transition from the OFF state to the PREHEAT state in response to detecting an HMG by outputting, as the state decision, the PREHEAT state, for example, when the controller 2105 detects the HMG while a current state of the heater engine is OFF. According to at least one example embodiment, the controller 2105 may control the heater engine 2215 to transition from the PREHEAT state to the ON state in response to detecting vaping (e.g., in response to detecting vapor drawing) while a current state of the heater engine is PREHEAT or OFF. According to at least some example embodiments, the amount of power supplied by the e-vapor device to the heater engine 2215 in the PREHEAT state is an amount that causes a temperature of the heater engine 2215 to be below a boiling point of a pre-vapor formulation material held in the a pre-vapor formulation compartment of the e-vapor device, and the amount of power supplied by the e-vapor device to the heater engine 2215 in the ON state is an amount that causes a temperature of the heater engine 2215 to be at or above the boiling point of the pre-vapor formulation material held in the a pre-vapor formulation compartment of the e-vapor device. The boiling point of the pre-vapor formulation material is a temperature of the heater engine 2215 at which the pre-vapor formulation material changes to a vapor.

Some period of time exists between a point when power is first supplied to a heater of an e-vapor device and a point when the heater has reached a temperature sufficient for the production of vapor. In at least some e-vapor devices, power is supplied to a heater of the e-vapor device only after vapor drawing is detected. Consequently, in such e-vapor device, there may be a substantial vapor latency. The term "vapor latency" refers a period of time between a point in time when an initial vapor drawing instance occurs and a point in time when an e-vapor device produces vapor.

According to at least some embodiments, the above-referenced vapor latency may be reduced or, alternatively, eliminated. For example, according to at least some example embodiments, the above-referenced vapor latency may be eliminated by being reduced to the point where the vapor latency is imperceptible or, alternatively, unnoticed. For example, the HMG is a gesture that may be expected to occur a relatively short time before vaping begins (i.e., before an initial vapor drawing instance occurs). Thus, according to at least some example embodiments, as a result of the above-referenced preheating operation in which power is supplied by the e-vapor device to the heater engine 2215 in response to detecting an HMG (i.e., before the initial vapor drawing instance occurs), the heater engine 2215 may achieve a temperature sufficient to generate vapor at or, alternatively, near the time when the initial vapor drawing instance occurs.

For example, when the controller 2105 controls the heater engine 2215 to transition from the PREHEAT state to the ON state in response to the detection of vapor drawing, an amount of time necessary to raise a temperature of the heater engine 2215 to the boiling point of the pre-vapor formulation material held in the a pre-vapor formulation compartment of the e-vapor device may be relatively small because a temperature of the heater engine 2215 will have already been raised as a result of the preheating operation that took place when the when the controller 2105 controlled the heater engine 2215 to transition to the PREHEAT state. Thus, when the heater engine 2215 transitions from the PREHEAT state to the ON state in response to the detection of a vapor drawing instance, the vapor latency may be effectively eliminated as a result of being reduced to an imperceptible or, alternatively, unnoticed level. Consequently, the preheating operation, according to at least some example embodiments, which occurs without the need for an adult vaper to activate any switches or buttons, may have a significant impact on the sensory experience of an adult vaper by reducing or, alternatively, eliminating the above-referenced vapor latency exhibited in some e-vapor device that lack such a preheating operation.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A method of controlling a heater of an e-vaping device, the heater having at least a first operation mode in which a first amount of power is supplied to the heater by the e-vaping device, and a second operation mode in which a second amount of power greater than the first amount is supplied to the heater by the e-vaping device, the method comprising:
   detecting, by the e-vaping device, movements of the e-vaping device;
   generating, by the e-vaping device, quaternions based on the detected movements;
   generating, by the e-vaping device, movement features based on the generated quaternions;
   applying, by the e-vaping device, the generated movement features to a classifier;
   determining whether a hand-to-mouth gesture (HMG) occurred with respect to the e-vaping device based on an output of the classifier; and
   transitioning the heater from the first operation mode to the second operation mode in response to determining that the HMG occurred,
   wherein the first operation mode is a mode in which no power is supplied to the heater by the e-vaping device, and the second operation mode is a mode in which an amount of power supplied to the heater by the e-vaping device is an amount that causes the heater to heat a pre-vapor formulation stored in the e-vaping device to a temperature below a boiling point of the pre-vapor formulation.

2. The method of claim 1, wherein the HMG is a gesture in which an adult vaper holding the e-vaping device moves their hand towards their mouth, and the classifier is trained to distinguish HMGs from other gestures.

3. The method of claim 2, wherein the classifier is a classifier that was generated through training using linear discriminant analysis (LDA).

4. The method of claim 1, further comprising:
   transforming the generated quaternions into three-dimensional (3-D) Cartesian coordinates.

5. The method of claim 4, wherein the generating movement features based on the generated quaternions comprises:
   extracting the movement features based on the 3-D Cartesian coordinates.

6. The method of claim 5, further comprising:
   filtering the 3-D Cartesian coordinates,
   the extracting including extracting the movement features from the filtered 3-D Cartesian coordinates.

7. The method of claim 5, further comprising:
   filtering the generated quaternions,
   the transforming including transforming the filtered quaternions into the 3-D Cartesian coordinates,
   the extracting including extracting the movement features from the 3-D Cartesian coordinates.

8. The method of claim 1, wherein the generated movement features comprise:
   a linear speed of the e-vaping device, and
   a distance from a rest point location of the e-vaping device.

9. The method of claim 8, wherein the distance from rest point location of the e-vaping device is a distance between a current location of the e-vaping device and a rest point of the e-vaping device, the rest point being a point in three-dimensional (3-D) space at which the e-vaping device was last stationary or substantially stationary.

10. The method of claim 1, wherein the detecting movements of the e-vaping device includes detecting the movements of the e-vaping device using device sensors included in the e-vaping device, the device sensors including at least one of a gyroscope, an accelerometer, and a magnetometer.

11. The method of claim 10, wherein the detecting movements of the e-vaping device includes detecting the movements of the e-vaping device using an inertial measurement unit (IMU) included in the e-vaping device.

* * * * *